US011390908B2

(12) United States Patent
Pederson et al.

(10) Patent No.: US 11,390,908 B2
(45) Date of Patent: Jul. 19, 2022

(54) DETECTION OF GENE LOCI WITH CRISPR ARRAYED REPEATS AND/OR POLYCHROMATIC SINGLE GUIDE RIBONUCLEIC ACIDS

(71) Applicants: UNIVERSITY OF MASSACHUSETTS, Boston, MA (US); University of Central Florida Research Foundation, Inc., Orlando, FL (US)

(72) Inventors: Thoru Pederson, Worcester, MA (US); Hanhui Ma, Shrewsbury, MA (US); Li-Chun Tu, Worcester, MA (US); Ardalan Naseri, Orlando, FL (US); Maximilaan Huisman, Worcester, MA (US); Shaojie Zhang, Orlando, FL (US)

(73) Assignees: UNIVERSITY OF MASSACHUSETTS, Boston, MA (US); UNIVERSITY OF CENTRAL FLORIDA FOUNDATION, INC., Orlando, FL (US)

( * ) Notice: Subject to any disclaimer, the term of this patent is extended or adjusted under 35 U.S.C. 154(b) by 531 days.

(21) Appl. No.: 15/757,240

(22) PCT Filed: Sep. 1, 2016

(86) PCT No.: PCT/US2016/049945
§ 371 (c)(1),
(2) Date: Mar. 2, 2018

(87) PCT Pub. No.: WO2017/040813
PCT Pub. Date: Mar. 9, 2017

(65) Prior Publication Data
US 2019/0249230 A1 Aug. 15, 2019

Related U.S. Application Data

(60) Provisional application No. 62/277,216, filed on Jan. 11, 2016, provisional application No. 62/276,568, filed on Jan. 8, 2016, provisional application No. 62/213,351, filed on Sep. 2, 2015.

(51) Int. Cl.
*C12Q 1/6816* (2018.01)
*C12N 15/11* (2006.01)
*C07H 21/02* (2006.01)
*C12N 15/85* (2006.01)
*C12N 9/22* (2006.01)

(52) U.S. Cl.
CPC .......... *C12Q 1/6816* (2013.01); *C07H 21/02* (2013.01); *C12N 9/22* (2013.01); *C12N 15/11* (2013.01); *C12N 15/85* (2013.01); *C12N 2310/20* (2017.05); *C12N 2310/3519* (2013.01); *C12N 2830/003* (2013.01); *C12Q 2600/156* (2013.01)

(58) Field of Classification Search
CPC ..................................................... C12N 15/11
See application file for complete search history.

(56) References Cited

U.S. PATENT DOCUMENTS

| | | | | |
|---|---|---|---|---|
| 3,817,837 | A | 6/1974 | Rubenstein et al. | 435/7.9 |
| 3,850,752 | A | 11/1974 | Schuurs et al. | 435/7.93 |
| 3,939,350 | A | 2/1976 | Kronick et al. | 250/365 |
| 3,996,345 | A | 12/1976 | Ullman et al. | 436/537 |
| 4,275,149 | A | 6/1981 | Litman et al. | 435/7.91 |
| 4,277,437 | A | 7/1981 | Maggio | 422/401 |
| 4,366,241 | A | 12/1982 | Tom et al. | 435/7.91 |
| 6,203,986 | B1 * | 3/2001 | Singer | C07K 14/005 435/320.1 |
| 2015/0191744 | A1 * | 7/2015 | Wolfe | C12Q 1/6841 435/6.11 |
| 2019/0106693 | A1 * | 4/2019 | Rinn | C07H 21/02 |

FOREIGN PATENT DOCUMENTS

| | | |
|---|---|---|
| WO | WO/2013/144595 | 10/2013 |
| WO | WO/2015/048690 | 4/2015 |
| WO | WO/2015/089486 | 6/2015 |

OTHER PUBLICATIONS

Larson et al., Real-Time Observation of Transcription Initiation and Elongation on an Endogenous Yeast Gene, Apr. 2011, vol. 332, pp. 475-478 (Year: 2011).*
Bos et al. Tethered Function Assays as Tools to Elucidate the Molecular Roles of RNA-Binding Proteins, 2016, Adv Exp Med Biol., vol. 907, pp. 61-88 (Year: 2016).*
Livet et al. Transgenic strategies for combinatorial expression of fluorescent proteins in the nervous system, 2007, Nature, vol. 450, pp. 56-62 (Year: 2007).*
Zalatan et al. Engineering Complex Synthetic Transcriptional Programs with CRISPR RNA Scaffolds. 2015. Cell. Jan. 15; 160(0): 339-350 (Year: 2015).*

(Continued)

*Primary Examiner* — Nancy J Leith
*Assistant Examiner* — Tiffany Nicole Grooms
(74) *Attorney, Agent, or Firm* — Medlen & Carroll, LLP

(57) ABSTRACT

A C9orf72 DNA repeat expansion can be detected using a CRISPR Arrayed Repeat Detection System (CARDS). Based upon the compositions and methods supporting this platform primary cell cultures and/or blood cell smears can be tested under conventional clinical diagnostic laboratory conditions to diagnose genetically-based diseases having DNA repeat expansions, including but not limited to ALS. dCas9 constructs are also contemplated as having fluorescent proteins bound to any or all stem loop sequences, wherein detection of a plurality of dCas9 constructs having different colored fluorescent proteins can simultaneously detect at least six (6) different gene target loci.

19 Claims, 28 Drawing Sheets
(27 of 28 Drawing Sheet(s) Filed in Color)
Specification includes a Sequence Listing.

(56) References Cited

OTHER PUBLICATIONS

Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Anton, T. et al. (2014) "Visualization of specific DNA sequences in living mouse embryonic stem cells with a programmable fluorescent CRISPR/Cas system," *Nucleus* 5(2), 163-172.
Austin, R. J. et al. (2002) "Designed Arginine-Rich RNA-Binding Peptides with Picomolar Affinity," *Journal of the American Chemical Society* 124(37), 10966-10967.
Benson, G. (1999) "Tandem repeats finder: a program to analyze DNA sequences," *Nucleic Acids Research* 27(2), 573-580.
Bertrand, E. et al. (1998) "Localization of ASH1 mRNA Particles in Living Yeast," *Molecular Cell* 2(4), 437-445.
Bhaya, D. et al. (2011) "CRISPR-Cas Systems in Bacteria and Archaea: Versatile Small RNAs for Adaptive Defense and Regulation," *Annual Reviev of Genetics* 45(1), 273-297.
Bikard, D. et al. (2013) "Programmable repression and activation of bacterial gene expression using an engineered CRISPR-Cas system," *Nucleic Acids Research* 41(15), 7429-7437.
Charpentier, E. et al. (2013) "Biotechnology: Rewriting a genome," *Nature* 495(7439), 50-51.
Chen, B. et al. (2013) "Dynamic imaging of genomic loci in living human cells by an optimized CRISPR/Cas system," *Cell* 155(7), 1479-1491.
Cheng, A. W. et al. (2013) "Multiplexed activation of endogenous genes by CRISPR-on, an RNA-guided transcriptional activator system," *Cell Research* 23(16), 1163-1171.
Cho, S. W et al. (2013) "Targeted genome engineering in human cells with the Cas9 RNA-guided endonuclease," *Nature Biotechnology* 31(3), 230-232.
Ciuffi, A. et al. (2006) "Integration Site Selection by HIV-Based Vectors in Dividing and Growth-Arrested IMR-90 Lung Fibroblasts," *Molecular Therapy* 13(2), 366-373.
Cong, L. et al. (2013) "Multiplex Genome Engineering Using CRISPR/Cas Systems," *Science* (New York, N. Y.) 339(6121), 819-823.
Dahlman, J. E. et al. (2015) "Orthogonal gene knockout and activation with a catalytically active Cas9 nuclease," *Nature Biotechnology* 33, 1159.
Daigle, N. et al. (2007) "λN-GFP: an RNA reporter system for live-cell imaging," *Nature Methods* 4, 633.
Dean, K. M. et al. (2014) "Advances in fluorescence labeling strategies for dynamic cellular imaging," *Nature Chemical Biology* 10, 512.
DeJesus-Hernandez, M. et al. (2011) "Expanded GGGGCC Hexanucleotide Repeat in Noncoding Region of C9ORF72 Causes Chromosome 9p-Linked FTP and ALS," *Neuron* 72(2), 245-256.
Esvelt, K. M. et al. (2013) "Orthogonal Cas9 Proteins for RNA-Guided Gene Regulation and Editing," *Nature Methods* 10(11), 10.1038/nmeth.2681.
Eymery, A. et al. (2010) "Heat shock factor 1 binds to and transcribes satellite II and III sequences at several pericentromeric regions in heat-shocked cells," *Experimental Cell Research* 376(11), 1845-1855.
Fu, Y. et al. (2014) "Improving CRISPR-Cas nuclease specificity using truncated guide RNAs," *Nature Biotechnology* 32(3), 279-284.
Gilbert, L. A. et al. (2013) "CRISPR-mediated modular RNA-guided regulation of transcription in eukaryotes," *Cell* 154(2), 442-451.
Hou, Z. et al. (2013) "Efficient genome engineering in human pluripotent stem cells using Cas9 from Neisseria meningitidis," *Proceedings of the National Academy of Sciences* 110(39), 15644-15649.
Hsu, P. D. et al. (2014) "Development and applications of CRISPR-Cas9 for genome engineering," *Cell* 157(6), 1262-1278.
Hsu, P. D. et al. (2013) "DNA targeting specificity of RNA-guided Cas9 nucleases," *Nature Biotechnology* 31(9), 827-832.

Jacobson, M. R. et al. (1997) "Chapter 18—RNA Traffic and Localization Reported by Fluorescent Molecular Cytochemistry in Living Cells," in *mRNA Formation and Function* (Richter, J. D., Ed.), pp. 341-359, Academic Press, New York.
Jegou, T. et al. (2009) "Dynamics of telomeres and promyelocytic leukemia nuclear bodies in a telomerase-negative human cell line," *Molecular Biology of the Cell* 20(7), 2070-2082.
Jiang, F. et al. (2015) "A Cas9-guide RNA complex preorganized for target DNA recognition," *Science* 348(6242), 1477.
Jinek, M. et al. (2013) "RNA-programmed genome editing in human cells," *eLife 2*, e00471.
Kearns, N. A. et al. (2014) "Cas9 effector-mediated regulation of transcription and differentiation in human pluripotent stem cells," *Development* 141(1), 219-223.
Kiani, S. et al. (2015) "Cas9 gRNA engineering for genome editing, activation and repression," *Nature Methods* 12, 1051.
Kleinstiver, B. P. et al. (2015) "Engineered CRISPR-Cas9 nucleases with altered PAM specificities," *Nature* 523(7561), 481-485.
Konermann, S. et al. (2013) "Optical control of mammalian endogenous transcription and epigenetic states," *Nature* 500(7463), 472-476.
Konermann, S. et al. (2014) "Genome-scale transcriptional activation by an engineered CRISPR-Cas9 complex," *Nature* 517, 583.
La Spada, A. R. et al. (2010) "Repeat expansion disease: progress and puzzles in disease pathogenesis," *Nature Reviews Genetics* 11, 247.
Larson, M. H. et al. (2013) "CRISPR interference (CRISPRi) for sequence-specific control of gene expression," *Nature Protocols* 8(11), 2180-2196.
Ma, H et al. (2015) "Multicolor CRISPR labeling of chromosomal loci in human cells," *Proceedings of the National Academy of Sciences* 112(10), 3002.
Ma, H. et al. (2013) "Visualization of repetitive DNA sequences in human chromosomes with transcription activator-like effectors," *Proceedings of the National Academy of Sciences* 770(52), 21048-21053.
Maeder, M. L. et al. (2013) "CRISPR RNA-guided activation of endogenous human genes," *Nature Methods* 10(30), 977-979.
Mali, P. et al. (2013) "CAS9 transcriptional activators for target specificity screening and paired nickases for cooperative genome engineering," *Nature Biotechnology* 31(9), 833-838.
Mali, P. et al. (2013) "RNA-guided human genome engineering via Cas9," *Science* 339(6121), 823-826.
Marraffini, L. A. et al. (2010) "CRISPR interference: RNA-directed adaptive immunity in bacteria and archaea," *Nature Reviews Genetics* 11(3), 181-190.
Montini, E. et al. (2006) "Hematopoietic stem cell gene transfer in a tumor-prone mouse model uncovers low genotoxicity of lentiviral vector integration," *Nature Biotechnology* 24(6), 687-696.
Pennisi, E. (2013) "The CRISPR craze," *Science* 347(6148), 833-836.
Perez-Pinera, P. et al. (2013) "RNA-guided gene activation by CRISPR-Cas9-based transcription factors," *Nature Methods* 10(10), 973-976.
Qi, L. S. et al. (2013) "Repurposing CRISPR as an RNA-Guided Platform for Sequence-Specific Control of Gene Expression," *Cell* 152(5), 1173-1183.
Ran, F. A. et al. (2015) "In vivo genome editing using *Staphylococcus aureus* Cas9," *Nature* 520(7546), 186-191.
Ran, F. A. et al. (2013) "Double Nicking by RNA-Guided CRISPR Cas9 for Enhanced Genome Editing Specificity," *Cell* 154(6), 1380-1389.
Renton, Alan E. et al. (2011) "A Hexanucleotide Repeat Expansion in C9ORF72 Is the Cause of Chromosome 9p21-Linked ALS-FTD," *Neuron* 72(2), 257-268.
Shechner, D. M. et al. (2015) "Multiplexable, locus-specific targeting of long RNAs with CRISPR-Display," *Nature Methods* 12, 664.
Sorek, R. et al. (2013) "CRISPR-Mediated Adaptive Immune Systems in Bacteria and Archaea," *Annual Review of Biochemistry* 82(1), 237-266.
Tanenbaum, M. E. et al. (2014) "A Protein-Tagging System for Signal Amplification in Gene Expression and Fluorescence Imaging," *Cell* 159(3), 635-646.

(56) References Cited

OTHER PUBLICATIONS

Wiedenheft, B. et al. (2012) "RNA-guided genetic silencing systems in bacteria and archaea," *Nature* 482(7385), 331-338.
Zalatan, Jesse G. et al. (2015) "Engineering Complex Synthetic Transcriptional Programs with CRISPR RNA Scaffolds," *Cell* 160(1), 339-350.
Zhang, Y. et al. (2013) "Processing-Independent CRISPR RNAs Limit Natural Transformation in Neisseria meningitidis," *Molecular Cell* 50(4), 488-503.
PCT International Search Report of International Application No. PCT/US2016/049945 dated Mar. 20, 2017.
Ma, H. et al. (2016) "Multiplexed labeling of genomic loci with dCas9 and engineered sgRNAs using CRISPRainbow," *Nature Biotechnology* 34(5), 528-530.
Wang, S. et al. (2016) "An RNA-aptamer-based two-color CRISPR labeling system," *Scientific Reports* 6(1), 26857.
European Search Report for Application No. 16842996 dated Aug. 2, 2019.

\* cited by examiner

Figure 1A
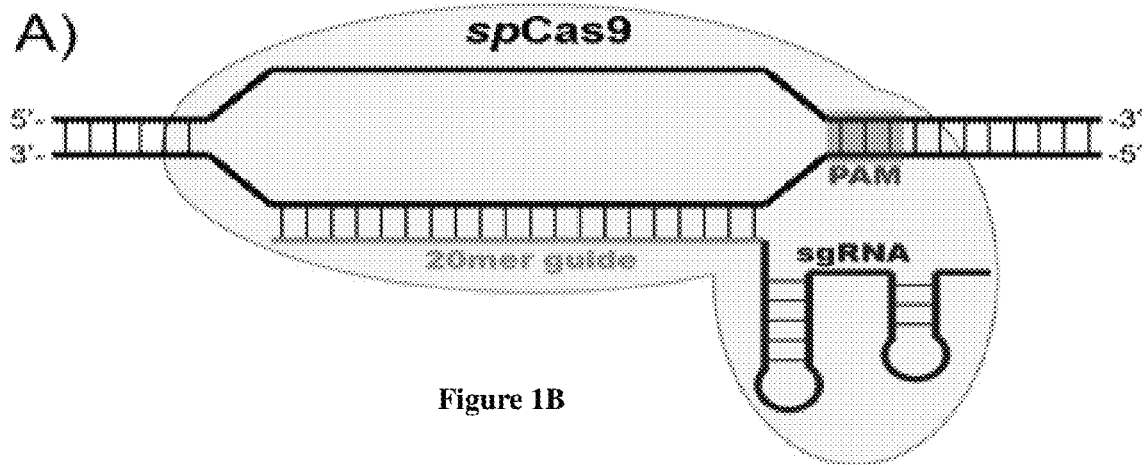
Figure 1B
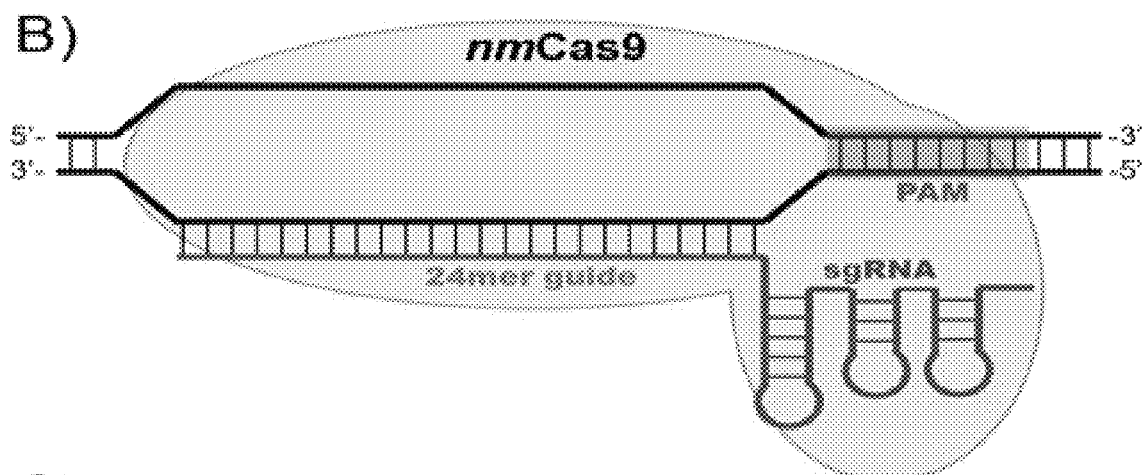
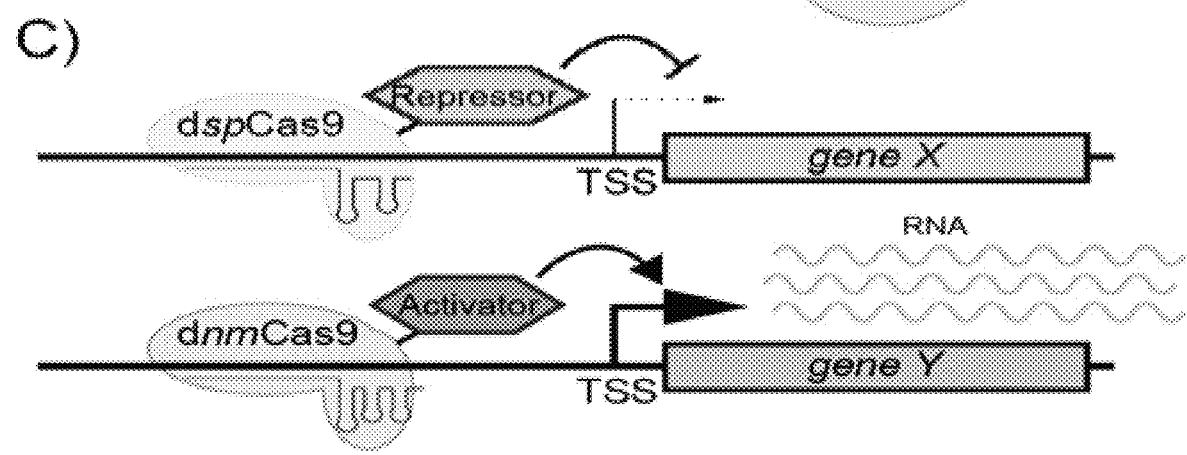
Figure 1C

Figure 11A
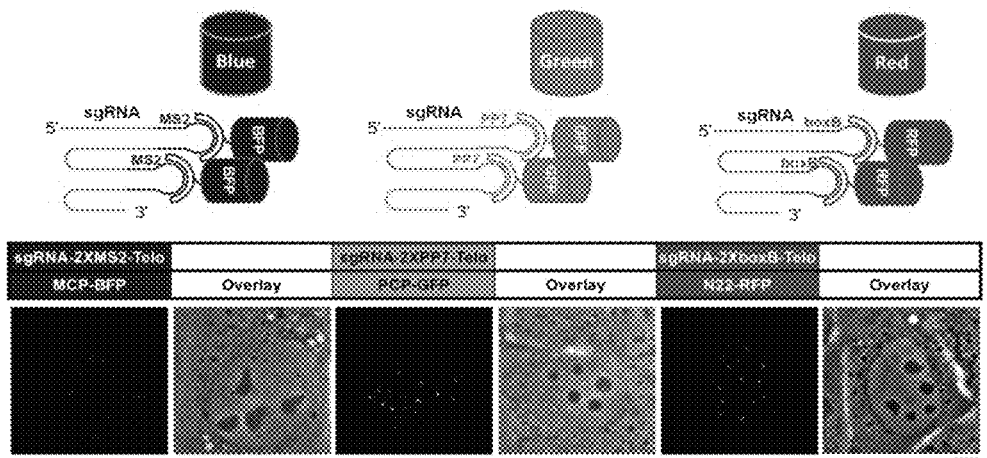
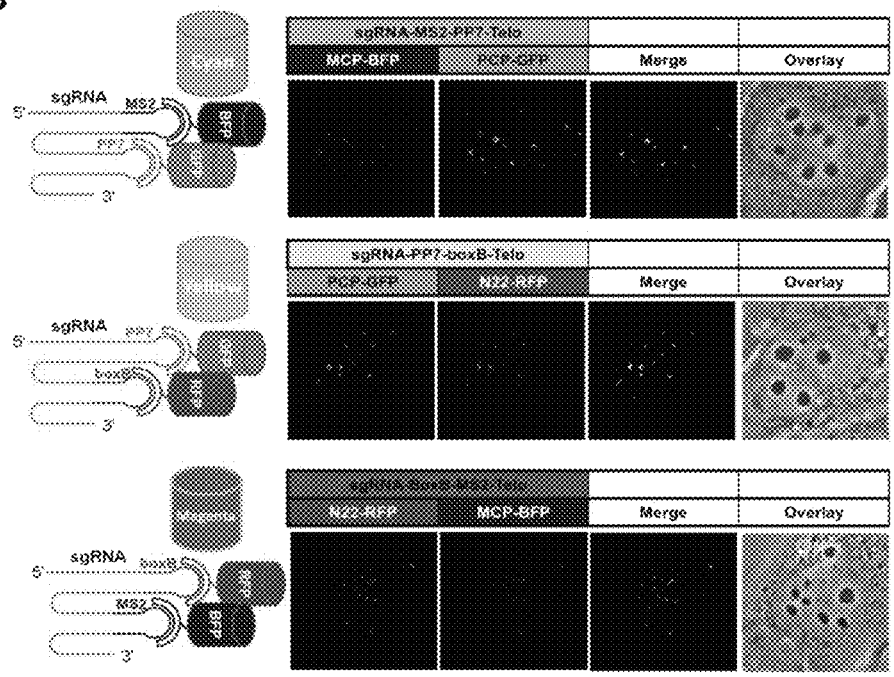
Figure 11B
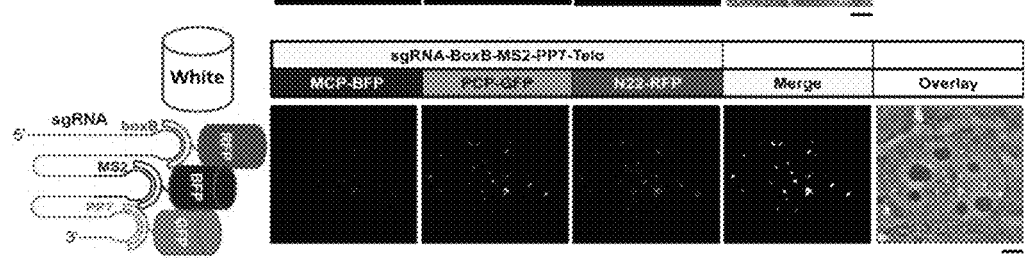
Figure 11C

Figure 12A
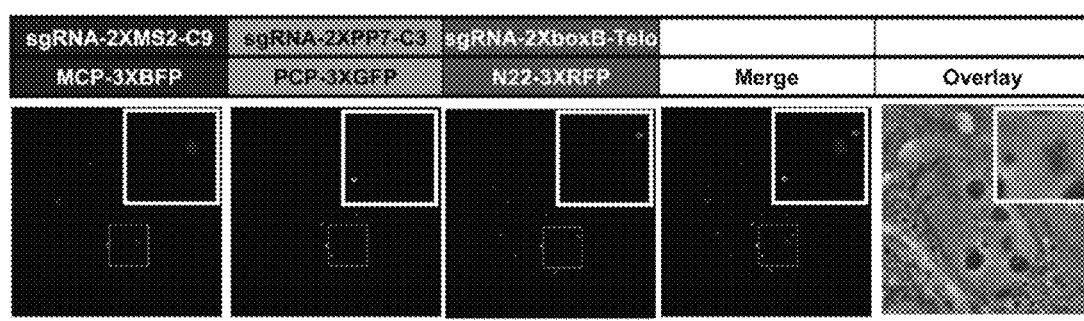
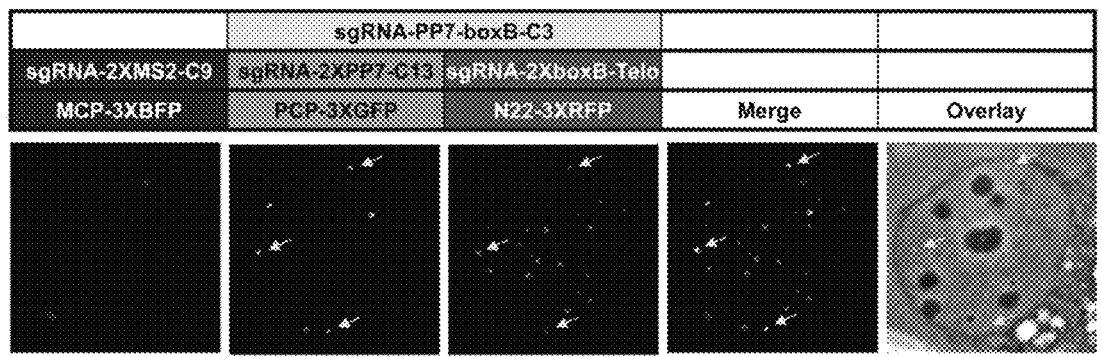
Figure 12B

Figure 16A
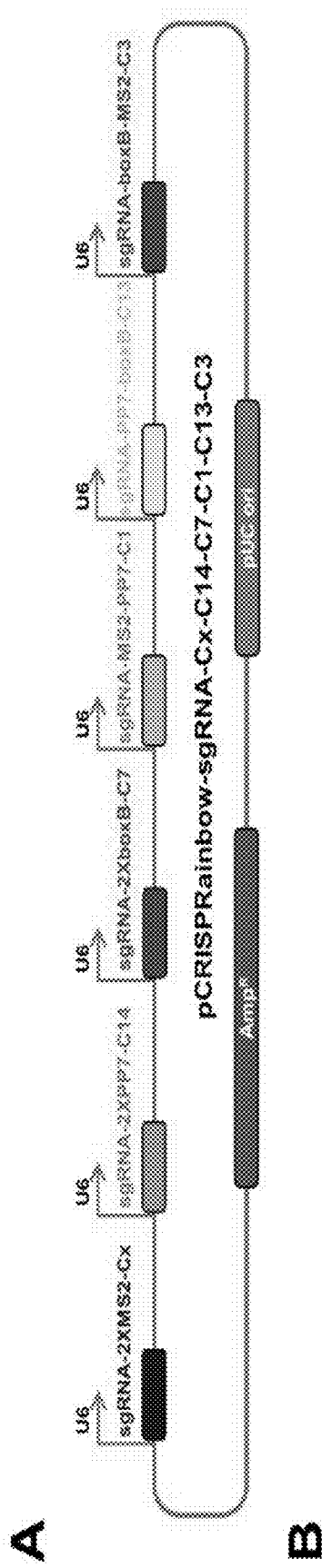
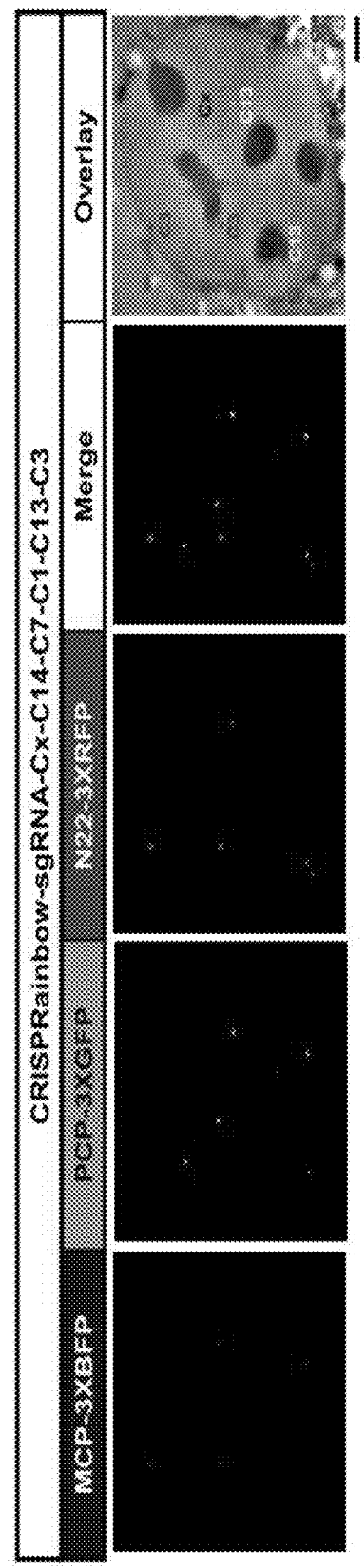
Figure 16B

A

B

DETECTION OF GENE LOCI WITH CRISPR ARRAYED REPEATS AND/OR POLYCHROMATIC SINGLE GUIDE RIBONUCLEIC ACIDS

STATEMENT REGARDING FEDERALLY SPONSORED RESEARCH OR DEVELOPMENT

This invention was made with government support under grant number GM102515 awarded by the National Institutes of Health. The Government has certain rights in the invention.

REFERENCE TO SEQUENCE LISTING SUBMITTED ELECTRONICALLY

The content of the electronically submitted sequence listing in ASCII text file, entitled "18416.txt", created Jan. 28, 2019, consisting of 102,785 bytes filed with the application is incorporated herein by reference in its entirety.

FIELD OF THE INVENTION

The present invention is related to the field of clinical diagnostics of genetic diseases. In particular, the genetic diseases are associated with repeat expansion sequences located in a non-coding region. A Clustered Regularly Interspaced Short Palindromic Repeat (CRISPR) sequence detection platform is provided that detects only the repeat expansion sequences. The CRISPR detection platform can diagnose genetic diseases using routine laboratory procedures within an hour of taking a biological sample. dCas9 constructs are also contemplated as having fluorescent proteins bound to any or all stem loop sequences, wherein detection of a plurality of dCas9 constructs having different colored fluorescent proteins can simultaneously detect at least six (6) different gene target loci.

BACKGROUND OF THE INVENTION

Recently, an RNA-guided adaptive immune system that is widespread in bacteria and archaea has been engineered for targeted DNA cleavage or gene regulation in prokaryotic and eukaryotic genomes. Wiedenheft, B. et al. (2012) "RNA-guided genetic silencing systems in bacteria and archaea," Nature 482(7385), 331-338; and Charpentier, E. and Doudna, J. A. (2013) "Biotechnology: Rewriting a genome," Nature 495(7439), 50-51. Such a system is generally referred to as Clustered Regularly Interspaced Short Palindromic Repeat (CRISPR).

This system combines RNA sequences and CRISPR-associated (Cas) proteins to generate a catalytic protein-RNA complex that utilize the associated RNA to generate sequence-specific double strand breaks at a complementary DNA sequence. A Cas9 nuclease from *Streptococcus pyogenes* (hereafter, Cas9 or spCas9) can be guided to specific sites in the human genome through base-pair complementation between a 20 nucleotide guide region of an engineered single guide RNA (sgRNA) and a genomic target sequence. Type II Cas9 orthologs from other species display similar properties, but have different specificities and CRISPR RNA sequences. Bhaya, D. et al. (2011) "CRISPR-Cas Systems in Bacteria and Archaea: Versatile Small RNAs for Adaptive Defense and Regulation," Annu. Rev. Genet. 45(1), 273-297; Mali, P. et al. (2013) "RNA-guided human genome engineering via Cas9," Science 339(6121), 823-826; Cho, S. W. et al. (2013) "Targeted genome engineering in human cells with the Cas9 RNA-guided endonuclease," Nat. Biotechnol. 31(3), 230-232; Cong, L. et al. (2013) "Multiplex genome engineering using CRISPR/Cas systems," Science 339(6121), 819-823; Jinek, M. et al. (2013) "RNA-programmed genome editing in human cells," eLife 2, e00471; and Esvelt et al. (2013). Orthogonal Cas9 proteins for RNA-guided gene regulation and editing. *Nature Methods*, 10(11), 1116-1121.

A catalytically-inactive programmable RNA-dependent DNA-binding protein (dCas9) can be generated by mutating the endonuclease domains within Cas9, which can modulate transcription in bacteria or eukaryotes either directly or through an incorporated effector domain. Qi, L. S. et al. (2013) "Repurposing CRISPR as an RNA-guided platform for sequence-specific control of gene expression," Cell 152 (5), 1173-1183; Bikard, D. et al. (2013) "Programmable repression and activation of bacterial gene expression using an engineered CRISPR-Cas system," Nucleic Acids Res. 41(15), 7429-7437; Gilbert, L. A. et al. (2013) "CRISPR-mediated modular RNA-guided regulation of transcription in eukaryotes," Cell 154(2), 442-451; Mali, P. et al. (2013) "CAS9 transcriptional activators for target specificity screening and paired nickases for cooperative genome engineering," Nat. Biotechnol. 31(9), 833-838; Konermann, S. et al. (2013) "Optical control of mammalian endogenous transcription and epigenetic states," Nature 500(7463), 472-476; Maeder, M. L. et al. (2013) "CRISPR RNA-guided activation of endogenous human genes," Nat. Meth. 10(10), 977-979; and Perez-Pinera, P. et al. (2013) "RNA-guided gene activation by CRISPR-Cas9-based transcription factors," Nat. Meth. 10(10), 973-976.

The detection and identification of specific DNA sequences can be performed by various methods in either live or fixed cells, for example, Fluorescence In Situ Hybridization (FISH). These methods have significant disadvantages including, but not limited to, preparation complications, lengthy assay times and lack of specificity. In FISH, the fixed cells must be subjected to a series of lengthy steps designed to: 1) permit penetration of the fluorescent oligonucleotides (by detergent permeabilization); 2) to denature the DNA; and 3) to facilitate oligonucleotide hybridization ("annealing"). These steps take 24-36 hours.

What is needed in the art is a method that provides compositions that provide significant improvements over the standard existing method for that is less costly and technically easier than FISH and can detect multiple mutated genes simultaneously in a single assay.

SUMMARY OF THE INVENTION

The present invention is related to the field of clinical diagnostics of genetic diseases. In particular, the genetic diseases are associated with repeat expansion sequences located in a non-coding region. A Clustered Regularly Interspaced Short Palindromic Repeat (CRISPR) sequence detection platform is provided that detects only the repeat expansion sequences. The CRISPR detection platform can diagnose genetic diseases using routine laboratory procedures within an hour of taking a biological sample. dCas9 constructs are also contemplated as having fluorescent proteins bound to any or all stem loop sequences, wherein detection of a plurality of dCas9 constructs having different colored fluorescent proteins can simultaneously detect at least six (6) different gene target loci.

In one embodiment, the present invention contemplates a composition comprising a labeled nuclease-dead Cas9 (dCas) protein and a single guide ribonucleic acid (sgRNA)

sequence that is complementary to at least a portion of a deoxyribonucleic acid repeat expansion sequence. In one embodiment, the deoxyribonucleic acid repeat expansion sequence is associated with a genetic disease. In one embodiment, the genetic disease results from a mutated c9orf72 gene. In one embodiment, the mutated c9orf72 gene results in amyotrophic lateral sclerosis. In one embodiment, the sgRNA sequence comprises a plurality of core repeat sequences. In one embodiment, the plurality of core repeat sequences comprises GGGGCC (SEQ ID NO: 1). In one embodiment, the plurality of core repeat sequences comprises CCCCGG (SEQ ID NO: 2). In one embodiment, the sgRNA is an sgRNA-W1 having a sequence of 5'-GCC-GGGGCC-GGGGCC-GGGGC-3' (SEQ ID NO: 3). In one embodiment, the sgRNA is an sgRNA-C1 having a sequence of 3'-CCCGG-CCCCGG-CCCCGG-GGG-5' (SEQ ID NO: 4). In one embodiment, the labeled dCas9 protein comprises a green fluorescent label. In one embodiment, the sgRNA comprises a plurality of fluorescent label binding sites. In one embodiment, the plurality of fluorescent label binding sites bind a green fluorescent protein.

In one embodiment, the present invention contemplates a method, comprising: a) providing; i) a biological sample obtained from a patient comprising a gene associated with a genetic disease, wherein said biological sample comprises a gene with at least one mutation and a deoxyribonucleic acid repeat expansion sequence; and ii) a composition comprising a labeled nuclease-dead Cas9 (dCas) protein and a single guide ribonucleic acid (sgRNA) sequence that is complementary to at least a portion of a deoxyribonucleic acid repeat expansion sequence; b) contacting said composition with said biological sample such that said labeled nuclease-dead Cas9 and sgRNA binds to said gene as a labeled nuclease-dead Cas9/sgRNA complex; c) detecting said labeled nuclease-dead Cas9/sgRNA complex on said gene; and d) diagnosing that said patient with said genetic disease. In one embodiment, the deoxyribonucleic acid repeat expansion sequence is associated with a genetic disease. In one embodiment, the mutated gene comprises a mutated c9orf72 gene. In one embodiment, the genetic disease is amyotrophic lateral sclerosis. In one embodiment, the sgRNA sequence comprises a plurality of core repeat sequences. In one embodiment, the plurality of core repeat sequences comprises GGGGCC (SEQ ID NO: 1). In one embodiment, the plurality of core repeat sequences comprises CCCCGG (SEQ ID NO: 2). In one embodiment, the sgRNA is an sgRNA-W1 having a sequence of 5'-GCC-GGGGCC-GGGGCC-GGGGC-3' (SEQ ID NO: 3). In one embodiment, the sgRNA is an sgRNA-C1 having a sequence of 3'-CCCGG-CCCCGG-CCCCGG-GGG-5' (SEQ ID NO: 4). In one embodiment, the labeled dCAS9 protein comprises a green fluorescent label. In one embodiment, the sgRNA comprises a plurality of fluorescent label binding sites. In one embodiment, the plurality of fluorescent label binding sites bind a green fluorescent protein.

In one embodiment, the present invention contemplates a kit comprising: a) a first container comprising a labeled nuclease-dead Cas9 (dCas) protein; b) a second container comprising a single guide ribonucleic acid (sgRNA) sequence that is complementary to at least a portion of a deoxyribonucleic acid repeat expansion sequence; c) a buffer that is compatible with said dCas9 protein and said sgRNA; and d) a sheet of instructions for detecting a deoxyribonucleic acid repeat expansion sequence associate with a genetic disease. In one embodiment, the deoxyribonucleic acid repeat expansion sequence is associated with a genetic disease. In one embodiment, the genetic disease comprises a mutated c9orf72 gene. In one embodiment, the mutated c9orf72 gene results in amyotrophic lateral sclerosis. In one embodiment, the sgRNA sequence comprises a plurality of core repeat sequences. In one embodiment, the plurality of core repeat sequences comprises GGGGCC (SEQ ID NO: 1). In one embodiment, the plurality of core repeat sequences comprises CCCCGG (SEQ ID NO: 2). In one embodiment, the sgRNA is an sgRNA-W1 having a sequence of 5'-GCC-GGGGCC-GGGGCC-GGGGC-3' (SEQ ID NO: 3). In one embodiment, the sgRNA is an sgRNA-C1 having a sequence of 3'-CCCGG-CCCCGG-CCCCGG-GGG-5' (SEQ ID NO: 4). In one embodiment, the labeled dCas9 protein comprises a green fluorescent protein. In one embodiment, the sgRNA comprises a plurality of fluorescent label binding sites. In one embodiment, the plurality of fluorescent label binding sites bind a green fluorescent protein. In some embodiments, the kits can optionally include enzymes capable of performing PCR (i.e., for example, DNA polymerase, Taq polymerase and/or restriction enzymes). In some embodiments, the kits may also optionally include appropriate systems (e.g. opaque containers) or stabilizers (e.g. antioxidants) to prevent degradation of the reagents by light or other adverse conditions. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In one embodiment, the present invention contemplates a composition comprising a nuclease-dead Cas9 (dCas) protein and a single guide ribonucleic acid (sgRNA) sequence comprising at least one fluorescent protein bound to at least one stem loop sequence. In one embodiment, each of said at least one fluorescent protein has a different color. In one embodiment, the different color is selected from the group consisting of red, green and blue. In one embodiment, each of the at least one stem loop sequence comprises an AU→GC mutation. In one embodiment, the at least one stem loop sequence includes, but is not limited to, an MS2 stem loop sequence, a PP7 stem loop sequence or a boxB stem loop sequence. In one embodiment, the at least one fluorescent protein includes, but is not limited to, an MCP-blue fluorescent protein, a PCP-green fluorescent protein or an N22-red fluorescent protein. In one embodiment, the MS2 stem loop sequence is bound to the MCP-blue fluorescent protein. In one embodiment, the PP7 stem loop sequence is bound to the PCP-green fluorescent protein. In one embodiment, the boxB stem loop sequence is bound to the N22-red fluorescent protein. In one embodiment, the sgRNA sequence comprises one fluorescent protein bound to one stem loop sequence. In one embodiment, the sgRNA sequence comprises two fluorescent proteins, wherein each fluorescent protein is bound to a different stem loop sequence. In one embodiment, the sgRNA sequence comprises three fluorescent proteins, wherein each fluorescent protein is bound to a different stem loop sequence.

In one embodiment, the present invention contemplates at method, comprising: a) providing; i) a biological sample comprising a plurality of chromosomes comprising at least one gene target loci; ii) a composition comprising a nuclease-dead Cas9 (dCas9) protein and a single guide ribonucleic acid (sgRNA) sequence comprising at least one fluorescent protein bound to at least one stem loop sequence;

b) contacting said composition with said plurality of chromosomes; c) forming a dCas9/sgRNA complex on said at least one gene target loci; d) detecting at least one color from said at least one fluorescent protein; and e) identifying said at least one gene target loci based upon said detected at least one color. In one embodiment, the at least one gene target loci includes, but is not limited to, two gene target loci, three gene target loci, four gene target loci, five gene target loci or six gene target loci. In one embodiment, the at least one color includes, but is not limited to, red, green, blue, cyan, yellow, magenta or white. In one embodiment, the identifying said at least one gene target loci is simultaneous. In one embodiment, each of said at least one fluorescent protein has a different color. In one embodiment, the different color is selected from the group consisting of red, green and blue. In one embodiment, each of the at least one stem loop sequence comprises an AU→GC mutation. In one embodiment, the at least one stem loop sequence includes, but is not limited to, an MS2 stem loop sequence, a PP7 stem loop sequence or a boxB stem loop sequence. In one embodiment, the at least one fluorescent protein includes, but is not limited to, an MCP-blue fluorescent protein, a PCP-green fluorescent protein or an N22-red fluorescent protein. In one embodiment, the MS2 stem loop sequence is bound to the MCP-blue fluorescent protein. In one embodiment, the PP7 stem loop sequence is bound to the PCP-green fluorescent protein. In one embodiment, the boxB stem loop sequence is bound to the N22-red fluorescent protein. In one embodiment, the sgRNA sequence comprises one fluorescent protein bound to one stem loop sequence. In one embodiment, the sgRNA sequence comprises two fluorescent proteins, wherein each fluorescent protein is bound to a different stem loop sequence. In one embodiment, the sgRNA sequence comprises three fluorescent proteins, wherein each fluorescent protein is bound to a different stem loop sequence.

In one embodiment, the present invention contemplates a kit comprising: a) a first container comprising a nuclease-dead Cas9 (dCas) protein; b) a second container comprising a single guide ribonucleic acid (sgRNA) sequence comprising at least one fluorescent protein bound to at least one stem loop sequence; c) a buffer that is compatible with said dCas9 protein and said sgRNA; and d) a sheet of instructions for detecting multiple gene target loci. In one embodiment, the at least one gene target loci includes, but is not limited to, two gene target loci, three gene target loci, four gene target loci, five gene target loci or six gene target loci. In one embodiment, the at least one color includes, but is not limited to, red, green, blue, cyan, yellow, magenta or white. In one embodiment, the identifying said at least one gene target loci is simultaneous. In one embodiment, each of said at least one fluorescent protein has a different color. In one embodiment, the different color is selected from the group consisting of red, green and blue. In one embodiment, each of the at least one stem loop sequence comprises an AU→GC mutation. In one embodiment, the at least one stem loop sequence includes, but is not limited to, an MS2 stem loop sequence, a PP7 stem loop sequence or a boxB stem loop sequence. In one embodiment, the at least one fluorescent protein includes, but is not limited to, an MCP-blue fluorescent protein, a PCP-green fluorescent protein or an N22-red fluorescent protein. In one embodiment, the MS2 stem loop sequence is bound to the MCP-blue fluorescent protein. In one embodiment, the PP7 stem loop sequence is bound to the PCP-green fluorescent protein. In one embodiment, the boxB stem loop sequence is bound to the N22-red fluorescent protein. In one embodiment, the sgRNA sequence comprises one fluorescent protein bound to one stem loop sequence. In one embodiment, the sgRNA sequence comprises two fluorescent proteins, wherein each fluorescent protein is bound to a different stem loop sequence. In one embodiment, the sgRNA sequence comprises three fluorescent proteins, wherein each fluorescent protein is bound to a different stem loop sequence. In some embodiments, the kits can optionally include enzymes capable of performing PCR (i.e., for example, DNA polymerase, Taq polymerase and/or restriction enzymes). In some embodiments, the kits may also optionally include appropriate systems (e.g. opaque containers) or stabilizers (e.g. antioxidants) to prevent degradation of the reagents by light or other adverse conditions. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In one embodiment, the present invention contemplates a composition comprising a nuclease-dead Cas9 (dCas) protein and a single guide ribonucleic acid (sgRNA) sequence that is complementary to at least a portion of a deoxyribonucleic acid repeat expansion sequence and at least one fluorescent protein bound to at least one stem loop sequence.

In one embodiment, the present invention contemplates at method, comprising: a) providing; i) a biological sample comprising a plurality of chromosomes comprising at least one gene target loci; ii) a composition comprising a nuclease-dead Cas9 (dCas9) protein and a single guide ribonucleic acid (sgRNA) sequence that is complementary to at least a portion of a deoxyribonucleic acid repeat expansion sequence and at least one fluorescent protein bound to at least one stem loop sequence; b) contacting said composition with said plurality of chromosomes; c) forming a dCas9/sgRNA complex on said at least one gene target loci; d) detecting at least one color from said at least one fluorescent protein; and e) identifying said at least one gene target loci based upon said detected at least one color.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing (e.g., autoantibody testing) to obtain further information on which to base a diagnosis.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

A "variant" of a protein is defined as an amino acid sequence which differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring *Bacillus anthracis* BclA.

A "substitution" results from the replacement of one or more nucleotides or amino acids by different nucleotides or amino acids, respectively.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide which retains essential biological characteristics.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "bind" and "binding" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

As used herein, the term "edit" "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target. Such a specific genomic target includes, but is not limited to, a chromosomal region, a gene, a promoter, an open reading frame or any nucleic acid sequence.

As used herein, the term "specific genomic target" refers to a pre-identified nucleic acid sequence of any composition and/or length. Such a specific genomic target includes, but is not limited to, a chromosomal region, a gene, a promoter, an open reading frame or any nucleic acid sequence. In some embodiments, the present invention interrogates these specific genomic target sequences with complementary sequences of sgRNA.

As used herein, the term "lentiviral vector" refers to a gene delivery vehicle adapted from lentiviruses, a subclass of Retroviruses. Lentiviruses have recently been adapted as gene delivery vehicles (vectors) thanks to their ability to integrate into the genome of non-dividing cells, which is the unique feature of Lentiviruses as other Retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides. The site of integration is unpredictable, which can pose a problem. The provirus can disturb the function of cellular genes and lead to activation of oncogenes promoting the development of cancer, which raises concerns for possible applications of lentiviruses in gene therapy. However, studies have shown that lentivirus vectors have a lower tendency to integrate in places that potentially cause cancer than gamma-retroviral vectors. Cattoglio, C. et al. (2007) "Hot spots of retroviral integration in human CD34+ hematopoietic cells," Blood 110(6), 1770-1778. More specifically, one study found that lentiviral vectors did not cause either an increase in tumor incidence or an earlier onset of tumors in a mouse strain with a much higher incidence of tumors. Montini, E. et al. (2006) "Hematopoietic stem cell gene transfer in a tumor-prone mouse model uncovers low genotoxicity of lentiviral vector integration," Nat. Biotechnol. 24(6), 687-696. Moreover, clinical trials that utilized lentiviral vectors to deliver gene therapy for the treatment of HIV experienced no increase in mutagenic or oncologic events. Ciuffi, A. et al. (2006) "Integration Site Selection by HIV-Based Vectors in Dividing and Growth-Arrested IMR-90 Lung Fibroblasts," Mol. Ther. 13(2), 366-373. Finally, non-integrating lentivirus can be created by utilizing a non-functional integrase gene, which facilitates the delivery of the viral genome to the target cell without incorporation into the host genome. For safety reasons lentiviral vectors never carry the genes required for their replication. To produce a lentivirus, several plasmids are transfected into a so-called packaging cell line, commonly HEK 293. One or more plasmids, generally referred to as packaging plasmids, encode the virion proteins, such as the capsid and the reverse transcriptase. Another plasmid contains the genetic material to be delivered by the vector. It is transcribed to produce the single-stranded RNA viral genome and is marked by the presence of the ψ (psi) sequence. This sequence is used to package the genome into the virion.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by 30 or so base pairs known as "spacer DNA". The spacers are short segments of DNA from a virus and may serve as a 'memory' of past exposures to facilitate an adaptive defense against future invasions. Marraffini, L. A. and Sontheimer, E. J. (2010) "CRISPR interference: RNA-directed adaptive immunity in bacteria and archaea," Nat. Rev. Genet. 11(3), 181-190.

As used herein, the term "Cas" or "CRISPR-associated (cas)" refers to genes often associated with CRISPR repeat-spacer arrays.

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence. Pennisi, E. (2013) "The CRISPR craze," Science 341(6148), 833-836.

As used herein, the term "nuclease deficient Cas9" refers to a modified Cas9 nuclease wherein the nuclease activity has been disabled by mutating residues in the RuvC and HNH catalytic domains. Disabling of both cleavage domains can convert Cas9 from a RNA-programmable nuclease into an RNA-programmable DNA recognition complex to deliver effector domains to specific target sequences. Qi, et al. (2013); and Gilbert, et al. (2013).

As used herein, the term "catalytically active Cas9" refers to an unmodified Cas9 nuclease comprising full nuclease activity.

As used herein, the term "effector domain" refers to a protein domain that can: 1) affect either transcriptional repression or activation, 2) catalytically modify histones, or 3) catalytically chemically modify DNA.

As used herein, the term "fluorescent protein" refers to a protein domain that comprises at least one organic compound moiety that emits fluorescent light in response to the appropriate wavelengths. For example, fluorescent proteins may emit red, blue and/or green light. Such proteins are readily commercially available including, but not limited to: i) mCherry (Clonetech Laboratories): excitation: 556/20 nm (wavelength/bandwidth); emission: 630/91 nm; ii) sfGFP (Invitrogen): excitation: 470/28 nm; emission: 512/23 nm; iii) TagBFP (Evrogen): excitation 387/11 nm; emission 464/23 nm.

As used herein, the term "sgRNA" refers to single guide RNA used in conjunction with CRISPR associated systems (Cas). sgRNAs contains nucleotides of sequence complementary to the desired target site. Watson-crick pairing of the sgRNA with the target site recruits the nuclease-deficient Cas9 to bind the DNA at that locus.

As used herein, the term "orthogonal" refers targets that are non-overlapping, uncorrelated, or independent. For example, if two orthogonal nuclease-deficient Cas9 gene fused to a different effector domains were implemented, they sgRNAs coded for each would not cross-talk or overlap. Not all nuclease-deficient Cas9 genes operate the same, which enables the use of orthogonal nuclease-deficient Cas9 gene fused to a different effector domains provided the appropriate orthogonal sgRNAs.

As used herein, the term "phenotypic change" or "phenotype" refers to the composite of an organism's observable characteristics or traits, such as its morphology, development, biochemical or physiological properties, phenology, behavior, and products of behavior. Phenotypes result from the expression of an organism's genes as well as the influence of environmental factors and the interactions between the two.

As used herein, the term "promoter" refers to a region of DNA that initiates transcription of a particular gene. Promoters are located near the genes they transcribe, on the same strand and upstream of the transcribed DNA (towards the 3' region of the anti-sense strand, also called template strand and non-coding strand).

As used herein, the term "constitutive promoter" refers to promoters that are active in all circumstances in the cell.

As used herein, the term "inducible promoter" or "regulated promoter" refers to promoters that become active in response to specific stimuli. For example, an inducible tetracycline promoter system (TetR) may be induced by the compound, doxycycline.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed to a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" is defined herein as an oligonucleotide sequence which exhibits greater than or equal to 50% identity to a sequence, when sequences having a length of 100 bp or larger are compared.

Low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^{3}$H, $^{125}$I $^{35}$S $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

BRIEF DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

The file of this patent contains at least one drawing executed in color. Copies of this patent with color drawings will be provided by the Patent and Trademark Office upon request and payment of the necessary fee.

FIGS. 1A-C shows a schematic overview of a CRISPR system.

FIG. 1A shows a S. pyogenes Cas9 (spCas9) that recognizes a target sequence through Watson-Crick pairing of 20 bases of the sgRNA and recognition of the neighboring PAM sequence (NGG) by the protein. Jinek, M. et al. (2012) "A Programmable Dual-RNA—Guided DNA Endonuclease in Adaptive Bacterial Immunity," Science 337(6096), 816-821.

FIG. 1B shows a N. meningitidis Cas9 (nmCas9) that utilizes a 24 base guide sequence in its sgRNA and the neighboring PAM sequence GANN (SEQ ID NO: 5) or NNNNGTTN (SEQ ID NO: 6)) for target recognition. Esvelt, K. M. et al. (2013) "Orthogonal Cas9 proteins for RNA-guided gene regulation and editing," Nat. Meth. 10(11), 1116-1121.

FIG. 1C shows a nuclease-dead dspCas9/sgRNA complex tethered to a repression domain that can be programmed for targeted down regulation of a single or set of genes (Gene X). This may be employed with an orthogonal nuclease-dead dnmCas9/sgRNA complex tethered to an activation domain for targeted upregulation of a different set of genes (Gene Y).

FIG. 5 presents exemplary data showing the detection of C9orf72 mutant repeats (>1000 repeats) in a fibroblast cell line derived from a patient with the neurodegenerative disease amyotrophic lateral sclerosis (ALS) using a dCas9-GFP protein.

FIG. 7 presents exemplary data showing signal-to-noise data in conventional red, green and blue dCAS9 probes. Chen B et al., Cell 155:1479 (2013); Ma et al., PNAS 112:3002 (2015); and Shechner et al., Nature Methods 12:664 (2015).

FIG. 11 presents exemplary data showing a wide spectrum of colors generated by embodiments of CRISPRainbow constructs.

FIG. 11(A): Primary colors for DNA labeling. Two MS2 (top left), two PP7 (top middle) or two boxB (top right) elements were inserted into a human telomere-specific sgRNA to generate primary colors. Shown beneath each sgRNA is live cell labeling of telomeres in human U2OS cells following co-expression of dCas9, the indicated sgRNA, and the cognate fluorescent protein. (The "overlay" images are on the live cell phase contrast micrographs in this and all other image figures in this paper.) Scale Bar: 5 µm.

FIG. 11(B): Secondary colors. MS2 and PP7 (top left), PP7 and boxB (middle left) or boxB and MS2 (bottom left) were inserted into the sgRNA so as to generate cyan, yellow or purple respectively, when bound by the cognate fluorescent proteins. Images at the right of each secondary color design are the telomere labeling images obtained after co-expression of dCas9, the indicated sgRNA, and the cognate pair of fluorescent proteins, Scale Bar: 5 µm.

FIG. 11(C): A tertiary "color". boxB, MS2 and PP7 were inserted into the sgRNA to generate white (left). Images at the right are telomere labeling following co-expression of dCas9, the triple element-bearing sgRNA, and the three cognate fluorescent proteins. Scale bar: 5 µm. Data in all panels are representative of experiments performed at least three times.

FIG. 12 presents exemplary data showing simultaneous labeling of multiple independent gene loci. Shown is a cell following co-expression of dCas9, the three sgRNAs and the cognate fluorescent proteins. Each repeated sequence was labeled by co-expression of dCas9, the three indicated sgRNAs, and the three cognate fluorescent proteins. Scale Bar: 5 µm. Data in all panels are representative of experiments performed at least three times.

FIG. 12(A): Simultaneous labeling of three (3) independent gene loci. MCP-3XBFP—A human chromosome 9 repeated sequence (blue). PCP-3XGFP—A human chromosome 3 repeated sequence (green). N22-3X RFP—A telomeric repeated sequence (red). Each repeated sequence was labeled by co-expression of dCas9, the three indicated sgRNAs, and the three cognate fluorescent proteins. Scale Bar: 5 µm.

FIG. 12(B): Simultaneous labeling of four (4) independent gene loci. MCP-3XBFP—A human chromosome 9 repeated sequence (blue). PCP-3XGFP—A human chromosome 13 repeated sequence (green). N22-3XRFP—A telomeric repeated sequence (red). PCP-3XGFP/N223XRFP—A human chromosome 3 repeated sequence (yellow).

FIG. 16 presents exemplary data showing the localization of six chromosome-specific loci simultaneously. Scale bar: 3 µm. Data in all panels are representative of experiments performed at least three times.

FIG. 16(A): Construct pCRISPRainbow-sgRNA-Cx-C14-C7-C1-C13-C3 for co-expression of six (6) sgRNAs each differentially labeled with a single, or combination of, fluorescent proteins.

FIG. 16(B): pCRISPRainbow-sgRNA-Cx-C14-C7-C1-C13-C3, dCas9, MCP-3XBFP, PCP-3XmNeonGreen and N22-3XRFP were co-transfected into U2OS cells. Each CRISPRainbow color was dedicated to one chromosome locus: blue for chromosome X, green for chromosome 14, red for chromosome 7, cyan for chromosome 1, yellow for chromosome 13 and magenta for chromosome 3 respectively.

FIG. 27A: Telomere detection of patient-derived fibroblast (FTD #26).

FIG. 27B: Detection of GGGGCC (SEQ ID NO: 1) (G4C2) telomeric repeats in an FTD patient-derived fibroblast.

DETAILED DESCRIPTION OF THE INVENTION

Figure 2:
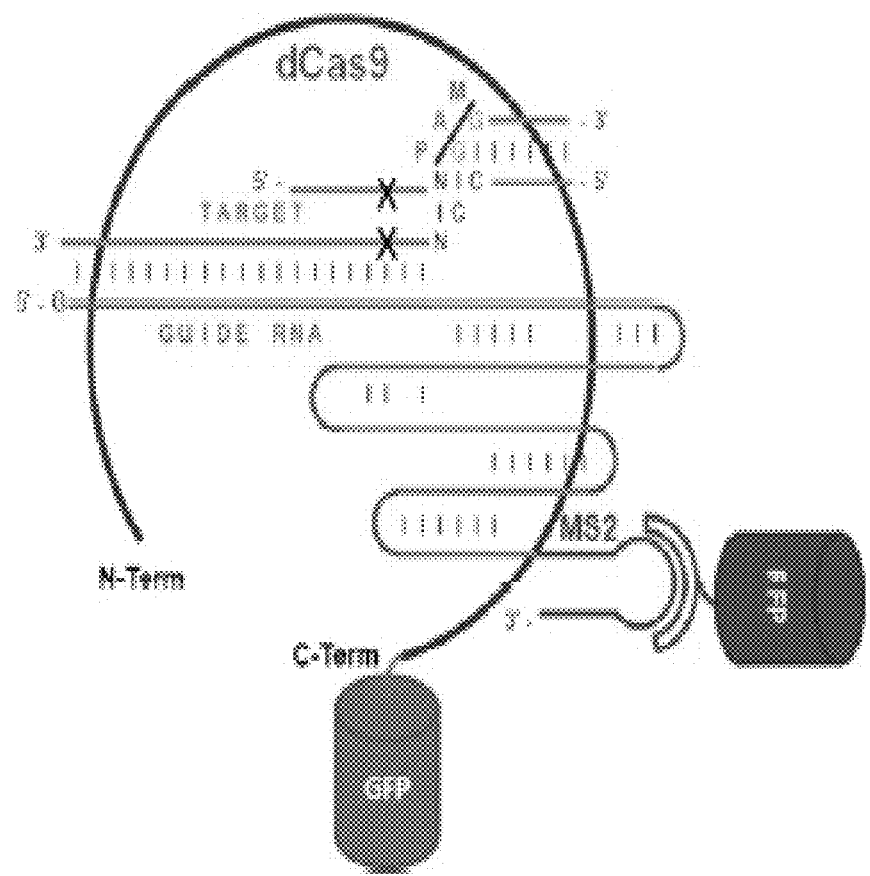
FIG. 2 presents one embodiment of DNA labeling by a CRISPR platform. Normally, Cas9 guided by an associated sgRNA, binds to a target DNA and cuts both strands ~3 nt to the left of the protospacer-adjacent motif (PAM). However, dCas9 lacks nuclease activity but still binds target DNA. By adding a GFP tag to a dCas9 or an MS2 tag to the sgRNA (for binding by fluorescent protein-tagged phage MS2 coat protein) the target DNA can be located in the cell nucleus.

The present invention is related to the field of clinical diagnostics of genetic diseases. In particular, the genetic diseases are associated with repeat expansion sequences located in a non-coding region. A Clustered Regularly Interspaced Short Palindromic Repeat (CRISPR) sequence detection platform is provided that detects only the repeat expansion sequences. The CRISPR detection platform can diagnose genetic diseases using routine laboratory procedures within an hour of taking a biological sample. dCas9 constructs are also contemplated as having fluorescent proteins bound to any or all stem loop sequences, wherein detection of a plurality of dCas9 constructs having different colored fluorescent proteins can simultaneously detect at least six (6) different gene target loci.

I. Clustered Regularly Interspaced Short Palindromic Repeat (CRISPR)

A. The CRISPR Platform

Clustered regularly interspaced short palindromic repeat (CRISPR) RNA sequences and CRISPR-associated (Cas) genes generate catalytic protein-RNA complexes that utilize the incorporated RNA to generate sequence-specific double strand breaks at a complementary DNA sequence. Bhaya et al., (2011). The Cas9 nuclease from *Streptococcus pyogenes* (hereafter, Cas9) can be guided to specific sites in the human genome through base-pair complementation between a 20 nucleotide guide region of an engineered single-guide RNA (sgRNA) and a genomic target sequence. Mali et al., (2013b); Cho et al., (2013); Cong et al., (2013); and Jinek et al., (2013). A catalytically-inactive programmable RNA-dependent DNA-binding protein (dCas9) can be generated by mutating the endonuclease domains within Cas9 which can modulate transcription in bacteria or eukaryotes either directly or through an incorporated effector domain. Qi et al., (2013); Bikard et al., (2013); Gilbert et al., (2013a); Mali et al., (2013a); Konermann et al., (2013); Maeder et al., (2013); and Perez-Pinera et al., (2013).

CRISPR-based defense systems are found broadly in bacterial and archaeal systems. Type II systems employ a single protein, Cas9, to facilitate RNA-guided cleavage of a target DNA sequence complementary to the sgRNA and the protospacer adjacent motif (PAM) recognized by Cas9, where both elements must be recognized to achieve efficient DNA cleavage. Sorek, R. et al. (2013) "CRISPR-Mediated Adaptive Immune Systems in Bacteria and Archaea," Annu. Rev. Biochem. 82(1), 237-266; and Hsu, P. D. et al. (2013) "DNA targeting specificity of RNA-guided Cas9 nucleases," Nat. Biotechnol. 31(9), 827-832, see also FIG. 1A.

The Cas9 nuclease from *S. pyogenes* (hereafter, spCas9) can be targeted to a specific sequence through Watson-Crick pairing between a 20 nucleotide guide region of an engineered single-guide RNA (sgRNA) and a target sequence. The *N. meningitidis* Cas9 (nmCas9) recognizes a larger PAM element and employs a different (orthogonal) guide RNA. Hou, Z. et al. (2013) "Efficient genome engineering in human pluripotent stem cells using Cas9 from *Neisseria meningitidis*," P.N.A.S. 110(39), 15644-15649; and Zhang, Y. et al. (2013) "Processing-Independent CRISPR RNAs Limit Natural Transformation in *Neisseria meningitidis*," Mol. Cell 50(4), 488-503; see also, FIG. 1B.

A catalytically-inactive programmable, RNA-dependent DNA-binding protein (the nuclease-dead versions of these Cas9 variants: dspCas9 or dnmCas9) can be generated by mutating the RuvC and HNH endonuclease domains within Cas9, which can modulate transcription in bacteria or eukaryotes either directly or through an incorporated effector domain. See, FIG. 1C.

Various systems involving CRISPR-Cas systems have been described. For example, a prokaryotic type II CRISPR-Cas systems can be adapted to enable targeted genome modifications across a range of eukaryotes. Mali, P. et al. (2013). The reference describes an engineered system to enable RNA-guided genome regulation in human cells by tethering transcriptional activation domains either directly to a nuclease-null Cas9 protein or to an aptamer-modified single guide RNA (sgRNA). Using this functionality a transcriptional activation-based assay was developed to determine the landscape of off-target binding of sgRNA:Cas9 complexes and compared it with the off-target activity of transcription activator-like effectors (TALEs).

A CRISPR-associated catalytically inactive Cas9 protein (dCas9) has been described that offers a general platform for RNA-guided DNA targeting. Gilbert, et al. (2013). Here, the reference describes that fusion of dCas9 to effector domains with distinct regulatory functions enables stable and efficient transcriptional repression or activation in human and yeast cells, with the site of delivery determined solely by a coexpressed short guide (sg)RNA. The reference employs a lentiviral delivery system to introduce the elements into the cells.

A single or a plurality of sgRNAs can direct dCas9 fused to a VP64 transcriptional activation domain to increase expression of endogenous human genes targeting gene transcriptional activation and repression in human cell lines and activation in *E. coli* cells. The results suggest that multiple or a plurality of sgRNA-dCas9-VP64 complexes can function efficiently together in a single cell. Maeder, et al. (2013).

It has been described that the use of a Cas9 nuclease mutant that retains DNA-binding activity and can be engineered as a programmable transcription repressor by preventing the binding of the RNA polymerase (RNAP) to promoter sequences or as a transcription terminator by blocking the running RNAP in bacteria. In addition, a fusion between the omega subunit of the RNAP and a Cas9 nuclease mutant directed to bind upstream promoter regions can achieve programmable transcription activation. Bikard, et al. (2013).

A catalytically dead Cas9 lacking endonuclease activity has been reported that when coexpressed with a guide RNA, generates a DNA recognition complex that can specifically interfere with transcriptional elongation, RNA polymerase binding, or transcription factor binding. This system, which is referred to as CRISPR interference (CRISPRi), can efficiently repress expression of targeted genes in *Escherichia coli*, with no detectable off-target effects. Qi, et al. (2013).

A catalytically dead Cas9 with a fused activation domain has been reported that when coexpressed with a guide RNA, generates a DNA recognition complex that can specifically activate transcriptional elongation of genes, but that 3 to 4 sgRNAs are required for robust activity. This system, which is referred to as CRISPR-on, was used to activate genes in mouse embryonic stem cells (mESCs), HeLa cells and mouse zygotes. Cheng, A. W. et al. (2013) "Multiplexed activation of endogenous genes by CRISPR-on, an RNA-guided transcriptional activator system," Cell Res. 23(10), 1163-1171.

A CRISPR targeting process has been described that relies on CRISPR components; is sequence-specific; and, upon simultaneous introduction of a plurality of custom guide RNA (gRNAs), can effect multiplex editing of target loci. The reference describes engineering the type II bacterial CRISPR system to function with custom (sgRNA) in human cells. For the endogenous AAVS1 locus, targeting rates of 10 to 25% in 293T cells was obtained, 13 to 8% in K562 cells, and 2 to 4% in induced pluripotent stem cells. The reference describes the results as establishing an RNA-guided editing tool for facile, robust, and multiplexable human genome engineering. Mali, et al. (2013).

An approach that combines a Cas9 nickase mutant with paired guide RNAs to introduce targeted double-strand breaks has also been reported. Ran, F. A. et al. (2013) "Double Nicking by RNA-Guided CRISPR Cas9 for Enhanced Genome Editing Specificity," Cell 154(6), 1380-1389. Because individual nicks in the genome are repaired with high fidelity, simultaneous nicking via appropriately offset guide RNAs is required for double-stranded breaks and extends the number of specifically recognized bases for target cleavage. The reference describes that using paired nicking can reduce off-target activity by 50- to 1,500-fold in cell lines and to facilitate gene knockout in mouse zygotes without sacrificing on-target cleavage efficiency. The reference speculates that the versatile strategy enables a wide variety of genome editing applications that require high specificity.

The use of a CRISPR-Cas system from Neisseria meningitides has been reported to demonstrate efficient targeting of an endogenous gene in three hPSC lines using homology-directed repair (HDR). The Cas9 RNA-guided endonuclease from N. meningitidis (NmCas9) recognizes a 5'-GATT-3' (SEQ ID NO: 7) protospacer adjacent motif (PAM) different from those recognized by Cas9 proteins from S. pyogenes and S. thermophilus (SpCas9 and StCas9, respectively). Similar to SpCas9, NmCas9 is able to use a single-guide RNA (sgRNA) to direct its activity. Because of its distinct protospacer adjacent motif, the N. meningitidis CRISPR-Cas machinery increases the sequence contexts amenable to RNA-directed genome editing. Hou, et al. (2013).

A "CRISPRi system" derived from the Streptococcus pyogenes CRISPR pathway has been reported that requires only the coexpression of a catalytically inactive Cas9 protein (lacking nuclease activity) and a customizable single guide RNA (sgRNA). The Cas9-sgRNA complex binds to DNA elements complementary to the sgRNA and causes a steric block that halts transcript elongation by RNA polymerase, resulting in the repression of the target gene. Larson, M. H. et al. (2013) "CRISPR interference (CRISPRi) for sequence-specific control of gene expression," Nat. Protoc. 8(11), 2180-2196.

II. dCas9 Sequence Detection Platform

Following its initial discovery in prokaryotic microbes, the CRISPR molecular machinery has been repurposed to allow operation in eukaryotic organisms (e.g., for example, mammals). Generally, two components are involved in the eukaryotic CRISPR system: a DNA endonuclease (Cas9; Cas for CRISPR-associated), and a short RNA sequence termed a single guide (sg) RNA. A ribonucleoprotein complex formed by the association of Cas9 and a sgRNA binds a double-stranded DNA sequence by virtue of sequence complementarity between the sgRNA and the desired target on one or the other DNA strand. A resulting displacement loop forms in the DNA then triggers the endonucleolytic action of Cas9. See, FIG. 2. In gene editing applications, a pair of such cuts is directed to flank the target gene, resulting in its resection.

However, when using a nuclease-inactive version of Cas9, termed dCas9 (d for nuclease-dead), and by attaching a fluorescent reporter to it, it is possible to deploy the CRISPR system as a probe to label specific genomic sequences in living eukaryotic cells. In contrast to the technique of fluorescence in situ hybridization (FISH)—a classical method of considerable utility for many purposes, CRISPR-based labeling offers an advantage of allowing specific chromosomal loci to be spatially mapped in the live cell, and also is very straightforward to carry out as it involves simple DNA transfection of the cells. In a recent further advance, multiple color versions of the CRISPR-based genomic labeling method were developed. Ma et al. Multicolor CRISPR Labeling of Chromosomal Loci in Human Cells. PNAS 112: 3202-3207 (2015).

In one embodiment, the present invention contemplates that a dCas9-GFP fusion protein may be produced by coupled in vitro transcription-translation from an appropriately designed DNA plasmid. In a separate reaction, a sgRNA is designed to recognize any desired target and is also transcribed from a suitable constructed DNA plasmid. Aliquots of a dCas9-GFP fusion protein and a properly targeted sgRNA are deposited on a cell culture attached to glass coverslips during growth and fixation (i.e., for example, 90% (v/v) methanol). The overlying liquid is then removed, the cells are subjected to a brief rinse with a buffer solution and then immediately examined in a fluorescence microscope.

For example, the present invention may utilize any one of a number of repetitive tandem repeat sequences. See, Table 1.

TABLE 1

Exemplary Types Of CRISPR Tandem Repetitive Targets

| Genomic Location | Repeat Sequence Template |
|---|---|
| Telomeres | TTAGGG (SEQ ID NO: 8) |
| Pericentromeric (Satellite II/III) | ATTCC (SEQ ID NO: 9) |
| Expansions | CTG; GGGGCC (SEQ ID NO: 1) |
| Subtelomeric/Acrocentric (chromosome specific) | 10-100 base pairs |

The present invention also provides compositions and methods for genomic sequence recognition using orthogonal Cas9 variants from three bacterial species; S. pyogenes, N. meningitidis (Nm) and S. thermophilus (St1) which have been used for editing and gene regulation in human cells without cross-talk in cognate sgRNA binding. Esvelt K M, et al. Orthogonal Cas9 proteins for RNA-guided gene regulation and editing. Nat. Methods 10(11): 1116-1121. See, Table 2.

TABLE 2

Cas9 Orthologs For Sequence Detection

| Cas9 Bacterial Source | Target DNA Sequence Size | sgRNA Source | PAM Sequences |
|---|---|---|---|
| S. pyogenese (Sp Cas9) | 9-20 mers | Sp sgRNA | NGG NAG NGT |
| N. meningitidis (Nm Cas9) | 20-24 mers | Nm sgRNA | NNNNGATT (SEQ ID NO: 10) NNNNGGTT (SEQ ID NO: 11) NNNGCTT (SEQ ID NO: 12) |

TABLE 2-continued

Cas9 Orthologs For Sequence Detection

| Cas9 Bacterial Source | Target DNA Sequence Size | sgRNA Source | PAM Sequences |
|---|---|---|---|
| S. thermophilus (St Cas9) | 20 mers | St1 sgRNA | NNAGAAW (SEQ ID NO: 13) NNGGAAW (SEQ ID NO: 14) NNAGGAW (SEQ ID NO: 15) NNAGGGW (SEQ ID NO: 16) |

Figure 3:
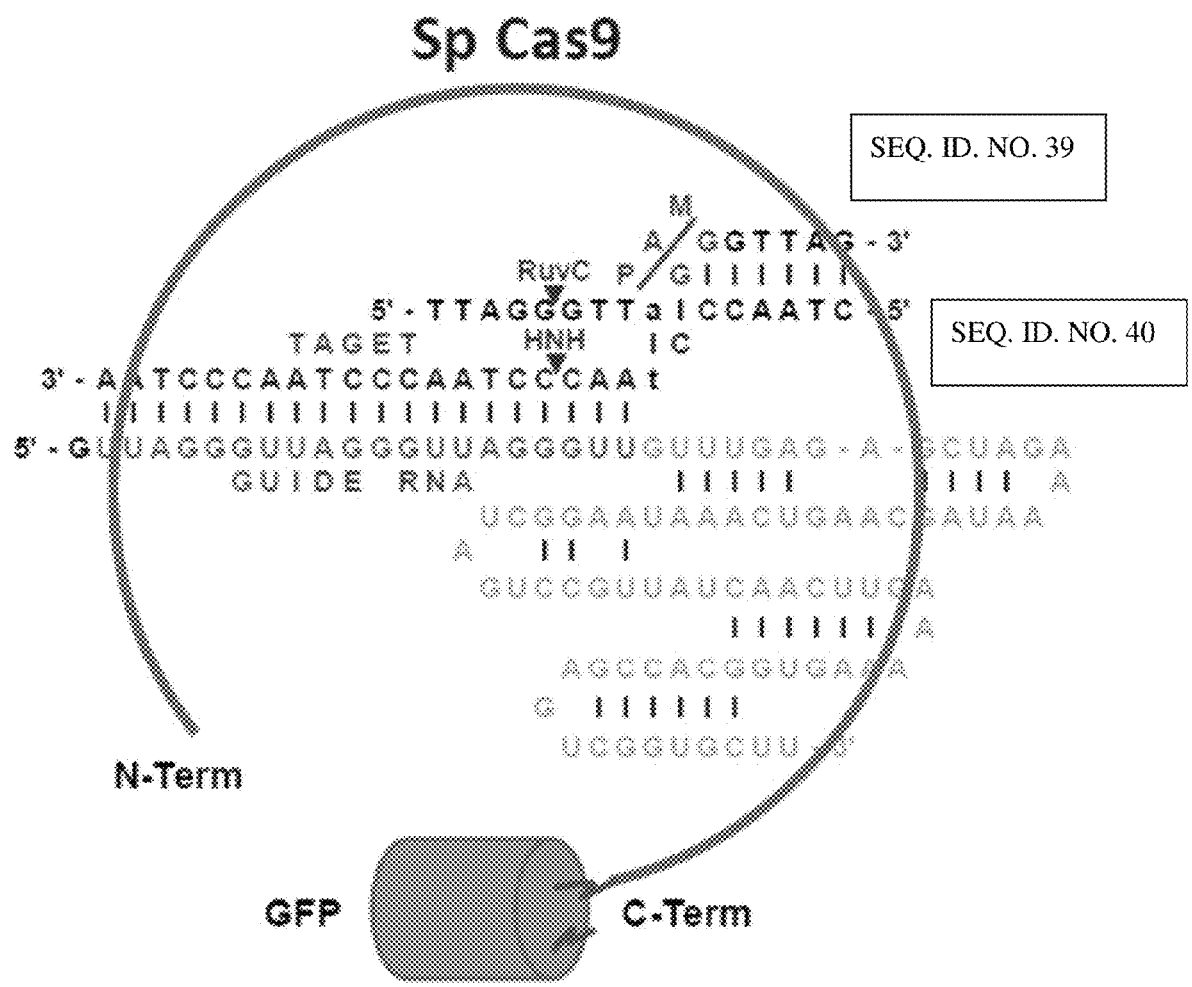
FIG. 3 illustrates one embodiment of an S. pyogenes Sp dCas9 binding configuration comprising a 20 mer target DNA sequence, an Sp sgRNA sequence and an NGG PAM sequence.

In one embodiment, a binding configuration of an *S. pyogenes* dCas9 comprises a 20 mer target DNA sequence, an Sp sgRNA sequence and an NGG PAM sequence. FIG. 3.

In some embodiments, the present invention contemplates a dCas9 nucleic acid detection method that has several advantages over conventional methods (e.g., FISH), in that: i) the present method can be completed in one hour; ii) all steps are carried out at ambient laboratory temperature and no special equipment of any kind is required; iii) the method can be performed by entry-level personnel with no specific background in molecular biology; iv) a separate detergent permeability step is unnecessary because the methanol fixation step renders the cells permeable to the dCas9 and sgRNA reagents; v) no DNA denaturation step is required since the CRISPR machinery recognizes double-stranded DNA; vi) the preparation of the two reagents (dCas9 and sgRNA) is very simple and fast relative to the preparation of fluorescent oligonucleotides, and/or less expensive than their purchase from commercial vendors; for example, the dCas9 coupled transcription-translation reaction takes one hour and the dCas9-GFP does not require purification but is used simply as an aliquot of the total reaction mix and the sgRNA is recovered from the transcription reaction by a simple one-step spin column; and vii) no lengthy annealing step is required since CRISPR binding to the DNA target in fixed cells is extremely rapid.

III. Polychromatic sgRNA Sequences

In one embodiment, the present invention contemplates a dCAS9 protein comprising an sgRNA sequence comprising at least one fluorescent label. In one embodiment, the dCAS9 protein comprises a plurality of fluorescent label binding sites. In one embodiment, the sgRNA sequence is bound to the at least one fluorescent label at an least one fluorescent label binding site. In one embodiment, the plurality of fluorescent label binding sites are located on dCAS9-MS2 binding sites.

In one embodiment, the present invention contemplates an sgRNA sequence comprising a plurality of stem loop sequences. In one embodiment, the sgRNA sequence binds to an at least one fluorescent label at said at least one sgRNA stem loop sequence. In one embodiment, the sgRNA sequence is bound to two fluorescent labels, wherein each of said two fluorescent labels are attached at a different stem loop sequence. In one embodiment, the sgRNA sequence is bound to three fluorescent labels, wherein each of said three labels are attached at a different stem loop sequence. In one embodiment, the fluorescent label has a color including, but not limited to, red, green and blue. In one embodiment, the fluorescent label is a green fluorescent protein. In one embodiment, the fluorescent protein is a red fluorescent protein. In one embodiment, the fluorescent protein is a blue fluorescent protein.

Determining gene and chromosome localization and their dynamics in live cells is believed to complement static, in situ approaches. In one embodiment, the present invention contemplates an in vivo DNA labeling system, "CRISPRainbow", comprising an sgRNA sequence bound to distinct sets of fluorescent proteins. Although it is not necessary to understand the mechanism of an invention, it is believed that the present invention combinatorially enhances a dCAS9 fusion protein spectral range by which multiple loci can be simultaneously visualized. For example, the data presented herein demonstrate that as many as six different chromosomal loci can be visualized simultaneously in a single living cell. This capability has found that tracking of multiple chromosomal loci in live cells shows that certain cells are quite restricted in their motion while other cells are far more extensive in their 3-D range.

The current emphasis of CRISPR technology is on gene editing and regulation. Hsu et al., *Cell* 157:1262-1278 (2014). In one embodiment, the present invention contemplates a method that applies CRISPR technology for labeling defined chromosomal loci as a way to resolve the 3-D genome in live cells. Chen et al., *Cell* 155:1479-91 (2013); Anton et al., *Nucleus* 5:163-172 (2014); and Ma et al., *Proc. Natl. Acad. Sci. USA* 112:3002-3007 (2015). Although it is not necessary to understand the mechanism of an invention, it is believed that the advantages of CRISPRainbow complements and extends information based on fluorescence in situ hybridization (FISH) conducted on fixed cells. For example, previous reports engineered three orthologous CRISPR systems for combined multi-color labeling of chromosomal loci in human cells. Ma et al., *Proc. Natl. Acad. Sci. USA* 112:3002-3007 (2015). The data presented herein introduces an entirely different and more expansive technology, in particular CRISPRainbow, that is based on a spectral range of fluorescently colored sgRNAs for simultaneously labeling multiple genomic loci.

Conventional sgRNAs were engineered for transcription regulation by addition of protein-interacting RNA aptamers for recruiting transcription factors or by carrying functional RNAs targeting to genomic loci. Zalatan et al., *Cell* 160:339-350 (2015); Konermann et al., *Nature* 517:583-588 (2015); and Shechner et al., *Nat Methods* 12:664-670 (2015). In some embodiments, the present invention contemplates improvements to these sgRNA scaffolds (e.g., sequences) that are adapted to recruit (e.g., for example, by either covalent and/or non-covalent binding) fluorescent proteins. In one embodiment, these fluorescent proteins are useful for imaging dCAS9-targeted cells.

CRISPRainbow is an advance that has novel advantages and enables new applications of the basic CRISPR platform. For example, challenges had remained for visualizing multiple genomic loci in live cells simultaneously by CRISPR-based approaches, notwithstanding an introduction of a multicolor CRISPR system based on orthogonal Cas9's. Ma et al., *Proc. Natl. Acad. Sci. USA* 112:3002-3007 (2015). In the conventional orthogonal Cas9 approach, each Cas9 requires different PAM sequences, which limits the range of target loci, plus the expression of the three Cas9s has to be balanced during multicolor labeling. Esvelt et al. *Nat. Methods* 10:1116-1121 (2013). Despite the recent reports using *S. aureus* Cas9, Cpf114 and SpCas9 variants, each having specific PAM sequences, even though they may expand the range of target sequence choice and might be amenable to the orthogonal Cas9-based multiple labeling system, their specificity and efficiency of DNA labeling need to be further determined. Ran et al., *Nature* 520:186-191 (2015); and Kleinstiver et al., *Nature* 523:481-485 (2015). In contrast, unlike orthogonal Cas9-based labeling, which requires a cognate sgRNA for each Cas9, in CRISPRainbow a single Cas9 is associated with variously colored sgRNAs. Thus, CRISPRainbow can be thought of as a "spectral code", and the full polychromatic range should be readily expandable, for example by use of yet a fourth RNA aptamer designed to be bound by, for example, a far-red fluorescent protein. Dean et al., *Nat. Chem. Biol* 10:512-523 (2014). In principle, adding even one more color to CRISPRainbow would extend the simultaneous live cell detection of genomic loci to fifteen (15) spectrally distinctive colors.

In some embodiments, the present invention contemplates short guide RNA sequences (e.g, close to seed sequence lengths) to facilitate efficient labeling. Jiang et al., *Science* 348:1477-1481 (2015). Although it is not necessary to understand the mechanism of an invention, it is believed that short guide RNA sequences should make it possible to deploy a nuclease-active Cas9 for labeling due to a lack of cleavage. Fu et al., *Nat. Biotechnol.* 32:279-284 (2014); Dahlman et al., *Nat. Biotechnol.* doi: 10.1038/nbt.3390 (2015); and Kiani et al., *Nat. Methods* doi: 10.1038/nmeth.3580 (2015). In such a format, one can envision a switchable CRISPR platform in which a live cell genomic loci labeling mode with Cas9, instead of dCas9, is then redirected to gene editing by simply changing the expressed sgRNA to a longer form.

A. Signal-To-Noise Considerations

Figure 7A:
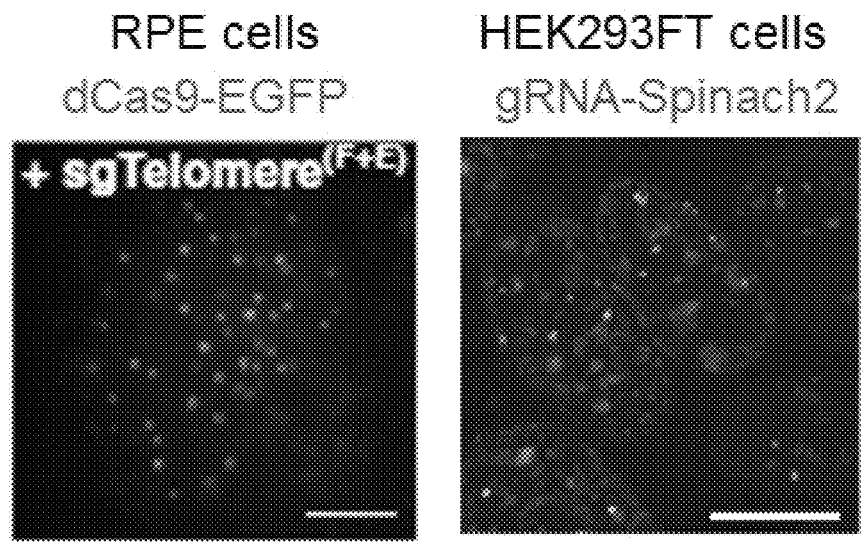
FIG. 7A: Live U2OS cell imaging of telomeric repeats using conventional probes of dCAS-EGFP (left panel) and gRNASpinach2.
Figure 7B:
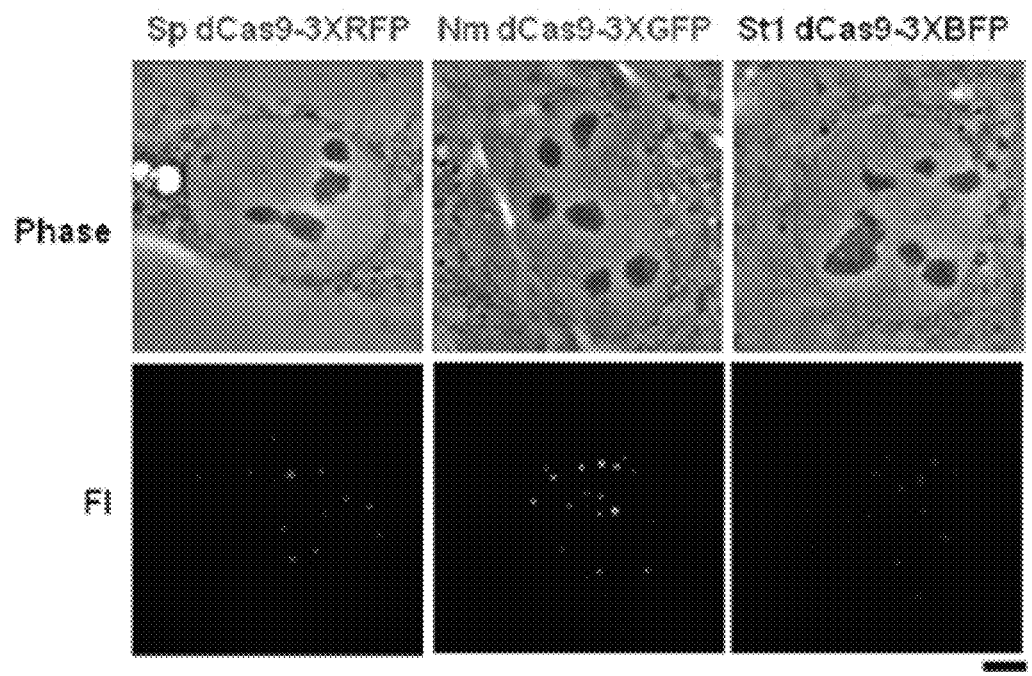
FIG. 7B: Live U2OS cell imaging of telomeric repeats using conventional CAS9 constructs of: i) dCAS9-sgRNA3xRFP (left panel); ii) dCAS9-sgRNA3xGFP (middle panel); and iii) dCAS9-sgRNA3xBFP (right panel).

Conventional sgRNA scaffolds used for gene editing proved to be inefficient for DNA labeling and had to be optimized by A→U mutations and stem loop extensions. Chen et al., *Cell* 155:1479-91 (2013); and FIG. 7A and FIG. 7B. Previous studies using boxB/λ N22 peptide pair used for RNA imaging showed inefficient DNA labeling in the CRISPRainbow system. Daigle et al., *Nat Methods* 4:633-636 (2007). It was also found that an affinity enhanced λ N22 peptide variant/boxB pair substantially increased the signal to noise ratio. Austin et al., *J. Am. Chem. Soc.* 124:10966-10967 (2002).

In some embodiments, the present invention contemplates replacing a sgRNA A-U pair with a sgRNA G-C pair in an sgRNA stem loop sequence. Although it is not necessary to understand the mechanism of an invention, it is believed that the A-U to G-C pair replacement results in improved signal to noise ratio as compared to conventional dCAS labeling sgRNAs without the necessity of stem loop extension.

B. Multi-Loci Differential Color Labeling

Figure 8:
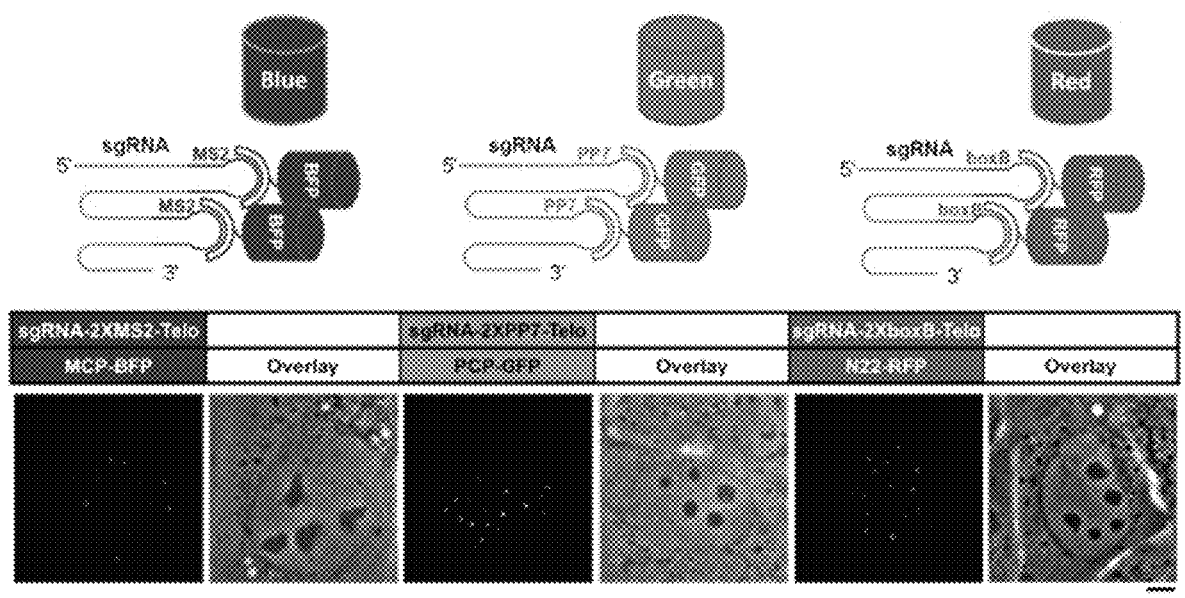
FIG. 8 presents exemplary data showing the construction and imaging of three embodiments of the CRISPRainbow primary color constructs: i) a blue fluorescent protein (MCP-BFP) attached to an sgRNA MS2 hairpin stem loop; ii) a green fluorescent protein (PCP-GFP) attached to an sgRNA PP7 hairpin stem loop; and iii) a red fluorescent protein (N22-RFP) attached to an sgRNA BoxB hairpin stem loop.
Figure 9:
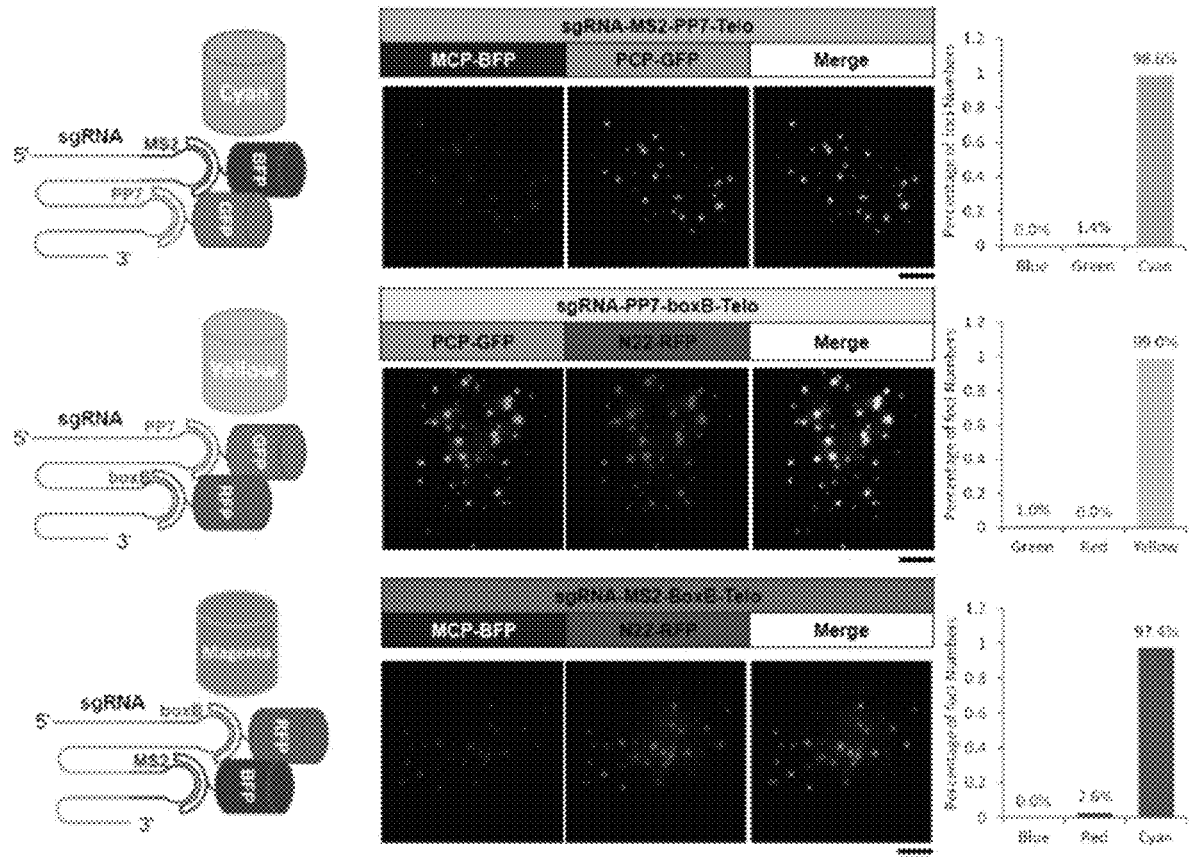
FIG. 9 presents exemplary data showing the construction and imaging of three embodiments of the CRISPRainbow secondary color constructs: i) cyan (MS2 MCP-BFP+PP7 PCP-GFP), ii) yellow (PP7 PCP-GFP+BoxB N22-RFP) or iii) magenta (BoxB N22-RFP+MS2 MCP-BFP).
Figure 10:
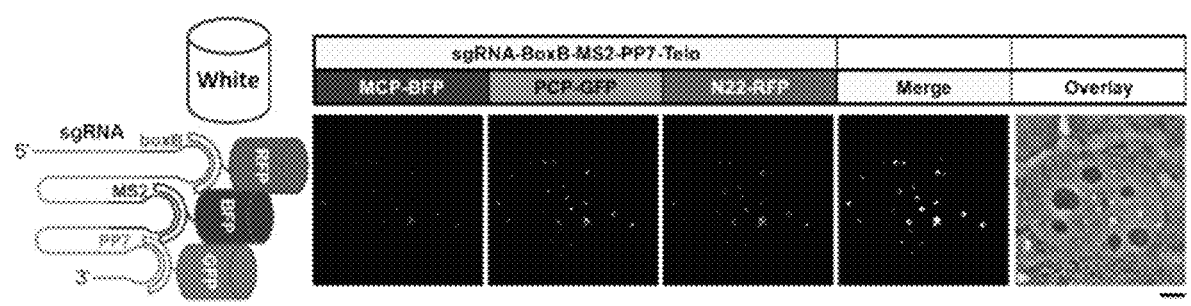
FIG. 10 presents exemplary data showing the construction and imaging of one embodiment of the CRISPRainbow tertiary color construct: white three (MS2 MCP-BFP+PP7 PCP-GFP+BoxB N22-RFP).

In one embodiment, the present invention contemplates an sgRNA sequence comprising an A-U pair to G-C pair mutation. In one embodiment, the mutated sgRNA sequence comprises at plurality of hairpin turns (e.g., stem loops). In one embodiment, the stem loops include, but are not limited to MS2, PP7 and BoxB. Daigle et al., *Nat Methods* 4:633-636 (2007). Although it is not necessary to understand the mechanism of an invention, it is believed that these hairpin turns can establish a broad spectral range for multi-loci labeling. For example, a variety of combinations of these hairpin turns are contemplated such that each sgRNA recruits a different pair of fluorescent proteins (FPs) recognizing two RNA elements. Such hairpin turn combinations can generate the following color combinations as a result of spectral overlapping: i) three primary colors—blue (MS2 MCP-blue fluorescent protein), green (PP7 PCP-green fluorescent protein) or red (BoxB N22-red fluorescent protein) when a single label is bound to an sgRNA sequence (FIG. 8); ii) three secondary colors—cyan (MS2 MCP-BFP+PP7 PCP-GFP), yellow (PP7 PCP-GFP+BoxB N22-RFP) or magenta (BoxB N22-RFP+MS2 MCP-BFP) when pairs of red, green or blue fluorescent proteins are bound to the same sgRNA (FIG. 9); and iii) white—when all three (MS2 MCP-BFP+PP7 PCP-GFP+BoxB N22-RFP) red, green and blue florescent proteins are bound to the same sgRNA sequence (FIG. 10). In one embodiment, the present invention contemplates generation of at least seven (7) fluorescent colors using an sgRNA labeled with a variety of fluorescent label combinations of red, green and blue colors.

The data shown herein depicts various strategies for introducing any one of the three primary colors onto an sgRNA and shows live cell images of telomere labeling. FIG. 11A. In contrast, improved labeling in live cells is observed when using a dual color CRISPRainbow labeled sgRNA. FIG. 11B. Labeling with an sgRNA labeled with all three primary colors is shown as white fluorescence. FIG. 11C.

To further evaluate the reliability of combinatorial colors in the CRISPRainbow system, z-stack images and maximum projections were assessed by capturing signals for pairs of fluorescent proteins simultaneously for the secondary colors. These data show that >97% of the telomere foci are labeled concurrently and that the brightness of each color at the same locus is highly correlative.

C. Multiple Site Labeling

To confirm the specificity of CRISPRainbow in its primary color mode, two distinct genomic loci were evaluated. In particular, telomeric sequences and repeated sequences in chromosome 9 (C9) were assayed. Repeat sequences were labeled with sgRNAs carrying hairpin stem loops including, but not limited to, MS2, PP7 or box B in pair-wise combinations, resulting in bi-color images. (data not shown). In another exemplification, these same two loci (telomeres and the C9 repeat) together with another repeated sequence in the subtelomeric region on the long arm of chromosome 3 (C3), were simultaneously visualized as three independent genomic loci. FIG. 12A. The telomeres and loci on C9 and C13 were readily labeled with the three primary colors (blue, green and red, respectively) while the locus on C3 was labeled by the fourth color, yellow, generated by the combination of green and red on that sgRNA. See, FIG. 12B. The same three loci as in FIG. 12A were targeted but with the C3 locus labeled in this case using a sgRNA carrying both the PP7 and boxB elements.

The simultaneous labeling of these four loci: e.g., telomere repeats, chromosome 3 (C3) repeats, chromosome 9 (C9) repeats, and chromosome 13 (C13) repeats were performed with short sgRNAs with an 11-mer guide RNA sequences for the C3 and C13 labeling because truncated sgRNAs significantly increase the signal to noise ratio compared to 20-mer guide RNA sequences for these two loci.

D. Nuclear Kinetics

Figure 13:
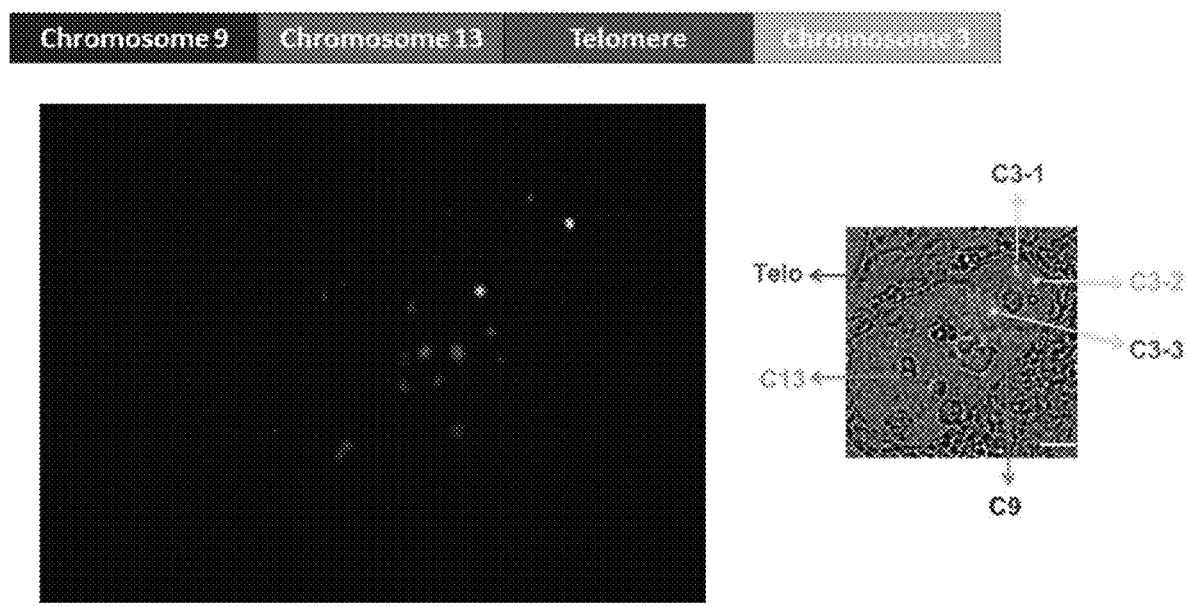
FIG. 13 presents exemplary data showing diversity in C3, C9, C13 and telomere range and direction movements.
Figure 14:
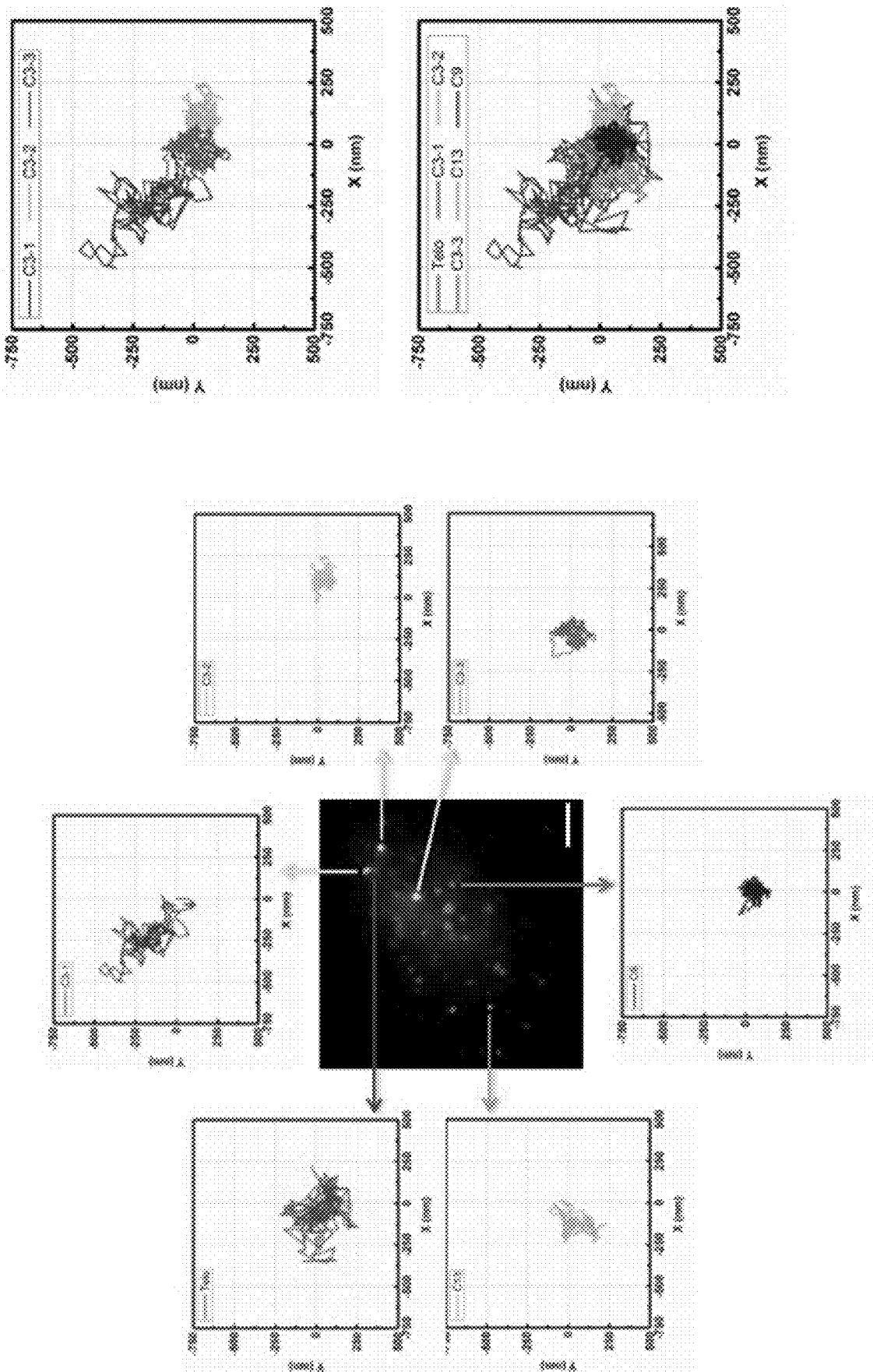
FIG. 14 presents exemplary data demonstrating live tracking of multiple DNA loci simultaneously. Unique sites in chromosome 3, 9 and 13 as well as telomeres were labeled simultaneously using the CRISPRainbow colors blue, green, red and yellow respectively. The exemplary data also show independent intrachromosomal movements for C3-1, C3-2 and C3-3. The movements of these loci were recorded at 50 ms per frame for 10 seconds (200 total frames). All trajectories were shifted to start from the origin (0, 0) for easy comparison of the movement vectors. Scale bar: 5 µm. Data are representative of experiments performed at least three times.

To interrogate the intranuclear dynamics of the above four loci in living cells, time-lapse microscopy was used to simultaneously track nuclear movements. The data show that the motion of different chromosomal loci is diverse in both range and direction. See, FIG. 13. Strikingly, the range of observed movement can vary even for different loci within a single chromosome, such as ~750 nm for C3-1 and ~250 nm for C3-2 and C3-3. FIG. 14.

Figure 15:
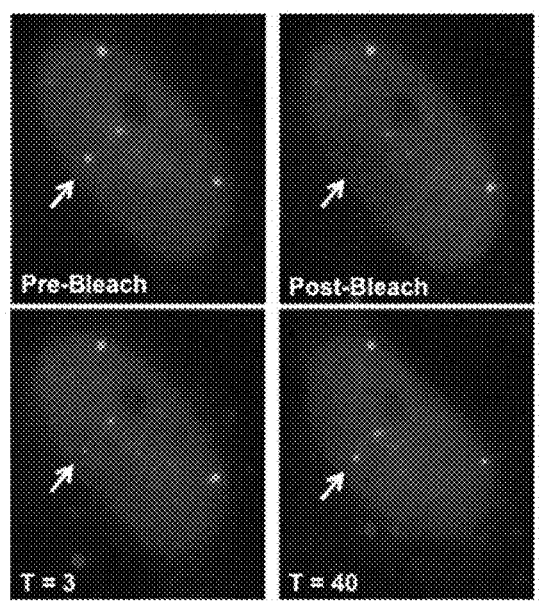
FIG. 15 presents exemplary data of photobleaching recovery for live cell imaging using a sgRNA-PP7 PCP-GFP dCAS9 construct.
Figure 15:
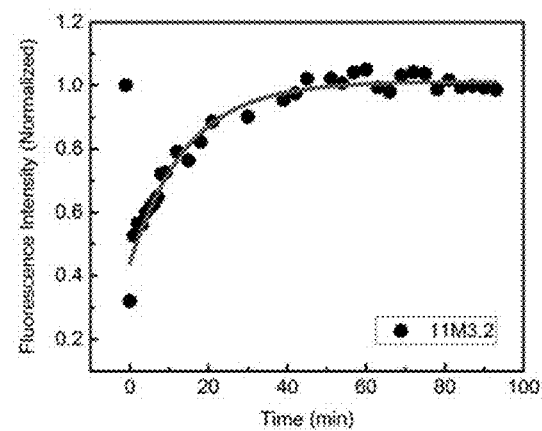

Although previous studies have tracked the movements of single chromosomal sites, such as telomeres or integrated lac operator arrays, CRISPRainbow offers the first opportunity to do so in a multiplex mode for a number of endogenous chromosomal loci. Jegou et al., *Mol. Biol. Cell* 20:2070-2082 (2009). Moreover, although the tracking results shown here were obtained over a very short interval, thus addressing instantaneous dynamics, with sufficient control over photobleaching, CRISPRainbow should enable longer term observations of the 3-D intranuclear positioning of various chromosomal sites, e.g. during progression through interphase, a program of cellular differentiation or in cases of translocations. See, FIG. 15.

E. HexaPlex Gene Loci Targeting

To exemplify the full potential of color range of CRISPRainbow, in one embodiment the present invention contemplates a method for labeling six distinct gene loci targets by detecting six CRISPRainbow sgRNA construct colors simultaneously. Gene loci targets located on chromosomes 1, 3, 7, 13, 14 and X, respectively, were chosen for each CRISPRainbow color using the color combination pattern of three primary colors and three secondary colors. To coordinate the expression of six sgRNAs in a single cell, a single plasmid was created to express all six sgRNAs. FIG. 16A. The location of each chromosomal site could be resolved by its expected CRISPRainbow color: blue for chromosome X, green for chromosome 14, red for chromosome 7, cyan for chromosome 1, yellow for chromosome 13 and magenta for chromosome 3. FIG. 16B.

IV. DNA Expansion Repeat Sequence Detection For Disease Diagnosis

The basis for the improved CRISPR platform described herein, is that the known utility for CRISPR labeling of specific genomic sequences can be modified to identify these sequences. Although it is not necessary to understand the mechanism of an invention, it is believed that such an improvement was possible because a dCas9:sgRNA complex binds double-stranded DNA and thus does not require a DNA denaturation step as is required for FISH. Moreover, it is believed that although a dCas9:sgRNA complex is larger than the oligonucleotides used in FISH, it is likely that after methanol fixation, the CRISPR complex is still able to cross cell membranes.

As an example of the advantages of a dCas9/DNA repeat expansion sequence targeted sgRNA method, it is to be noted that amyotrophic lateral sclerosis (ALS) is currently diagnosed by excluding all other neuromuscular diseases, which typically takes ~10 months. It has been estimated that ~10% of ALS patients (once diagnosed) have a c9orf72 repeat expansion. Thus, a rapid assay for such an expansion sequence that can be conducted upon the patient's first clinical visit, when ALS is only one of several possibilities, can accelerate the diagnosis of ALS. Many other repeat-expansion neuromuscular diseases are even more challenging and time-consuming to diagnose than ALS and the usefulness of the presently disclosed method for rapid assessment of these diseases is contemplated herein. La Spada et al. (2010) Repeat expansion disease: progress and puzzles in disease pathogenesis. Nat Rev Genet 11:247-258.

Figure 4:
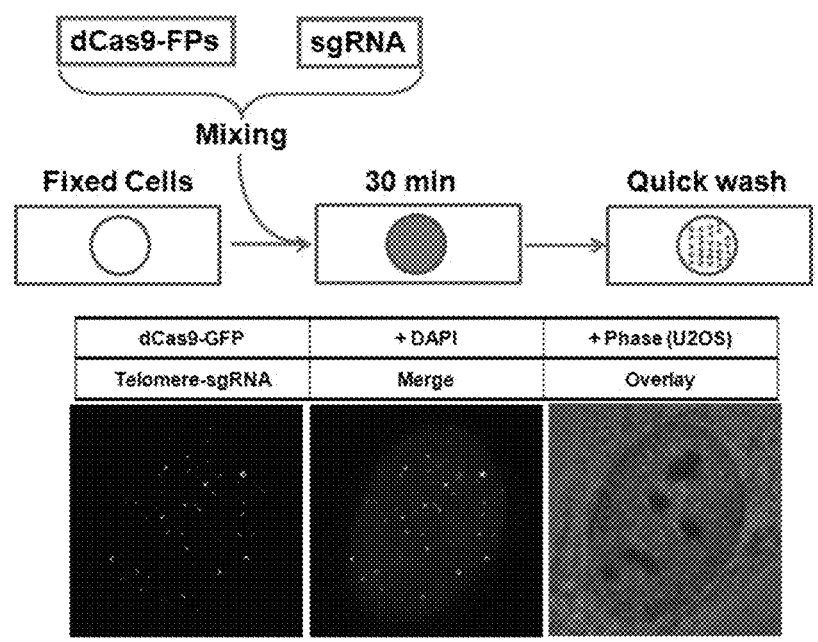
FIG. 4 presents exemplary data showing recognition of telomeric repeat sequences by customized sgRNA in human U2OS cells (an osteosarcoma cell line) using fluorescence imaging with a dCas9-GFP protein.

Preliminary data presented herein validates the presently disclosed method by showing the recognition of telomeric repeat sequences by repeat sequence-targeted sgRNA in human U2OS cells (an osteosarcoma cell line). After methanol fixation, incubation of the cells with the dCas9-GFP and sgRNA, followed by a brief wash fluorescence microscopy revealed a pattern of labeling that corresponded to CRISPR labeling of telomeres. See, FIG. 4.

In addition to performing the CARDS assay in human patient and normal subject fibroblasts, the present invention contemplates providing a blood smear cell sample. For example, blood smears can made from a line of transgenic mice bearing a BAC gene construct of human C9orf72 with 500 copies of the GGGGCC (SEQ ID NO: 1) repeat as well as their control line. These blood smears may be treated with methanol and then applied to the presently disclosed CARDS assay as described herein for fibroblasts. The frequency of the C9orf72 expansion signal among the white blood cells can be obtained through multiple experimental repeats and compared with the fibroblast data.

A. Detection of Amyotrophic Lateral Sclerosis (ALS) Expansion Repeat Sequences

The diagnosis of ALS is generally made by exclusion of other neurological diseases and consequently is difficult and time consuming. Therefore, improvements in this area are highly desirable.

Approximately 10% of ALS cases are caused by an elongation of the DNA in the gene C9orf72 and this represents causality for a large proportion of ALS patients. DeJesus-Hernandez et al. (2011). Expanded GGGGCC (SEQ ID NO: 1) hexanucleotide repeats in noncoding region of C9ORF72 causes chromosome 9p-linked FTD and ALS. Neuron 72:245-256; and Renton et al., (2011) A hexanucleotide repeat expansion in C9ORF72 is the cause of chromosome 9p21-linked ALS-FTD. Neuron 72:257-268. Although it is not necessary to understand the mechanism of an invention, it is believed that this gene mutation exists in these patients from birth and in all cells. This raises the possibility that the mutation can be detected in early stage in patients suspected of having the ALS mutation, and can be detected using a simple diagnostic composition.

CRISPR-FISH detection of ALS C9orf72 repeats using dCas9-GFP was tested in preliminary experiments where some drawbacks were identified, for example: 1) dCas9-GFP produced from an in vitro transcription/translation system was not able to quantify the optimal ratio of Cas9/sgRNA; and 2) the brightness and photostability of GFP should be comparable to other dyes, such as SNAP tag or HaloTag, which are also useful to detect the degree of ALS C9orf72 repeat expansion. Cas9-GFP, Cas9-SNAP and Cas9-HaloTag proteins were purified by a three-step purification including affinity column chromatography, ion exchange column chromatography and size exclusion chromatography to obtain a final product comprising pure and highly active Cas9 proteins.

Commercially available, self labeling tags, including but not limited to, SNAP tags and HaloTag dyes were also compared for relative brightness, background and sequence-specificity to determine DNA labeling efficiency. For example, SNAP tags included: 1) SNAP-Surface-954; 2) SNAP-Cell-505-Star, 3) SNAP-TMR-Star; 4) SNAP-Cell-Oregon Green; 5) SNAP-Cell-647-SiR (New England Biolabs). Other SNAP dyes were contributed from the HHMI Janelia Farm Research Campus, including: 1) Janelia-SNAP-JF549 and 2) Janelia-SNAP-JF646. Janelia also contributed two HaloTag dyes, for example: 1) Janelia-HaloTag-JF549 and 2) Janelia-HaloTag-JF646.

In one embodiment, the present invention contemplates a method comprising a CRISPR Arrayed Repeat Detection System (CARDS). In one embodiment, a C9orf72 mutation is detected in a patient cell using a simple benchtop laboratory test that takes only ~1 hour. The simplicity of this system underscores a distinct advantage over the current methods for detecting C9orf72 mutations. In one embodiment, the patient cells are derived from blood samples or oral lining cell samples (e.g., a buccal mucosal sample). Although it is not necessary to understand the mechanism of an invention, it is believed that the present invention vastly reduces the time and cost to diagnose ALS in patients with C9orf72 mutations as compared with the current methods. Most conventional diagnostic methods for ALS involve a combination of neurological symptomology assessments and laboratory procedures that can only be performed in specialized facilities and require several days for completion. Due to a lack of either a biomarker or a unique symptom that can be definitively associated with ALS, this disease is currently diagnosed by exclusion of all other neuromuscular conditions. Therefore, the diagnosis is a tedious process and takes on average ~10 months from the onset of initial symptoms.

Figure 5A:
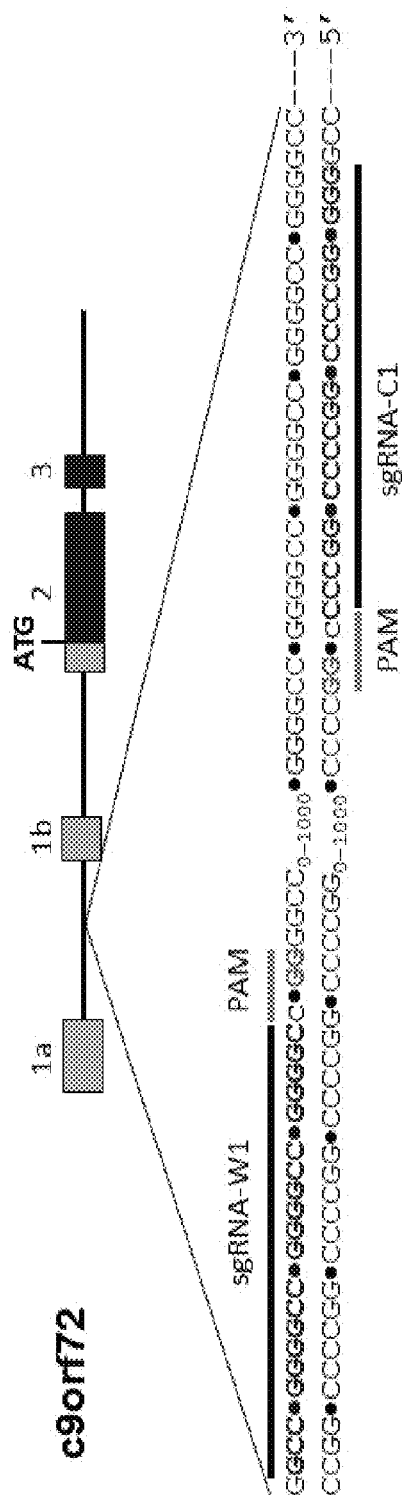
FIG. 5A: A design of a sgRNA targeting a C9orf72 gene hexanucleotide based upon one allele of an ALS c9orf72 gene that contains a very long expansion sequence comprising greater than 1000 repeats of the hexanucleotide GGGGCC (SEQ ID NO: 1).
Figure 5B:
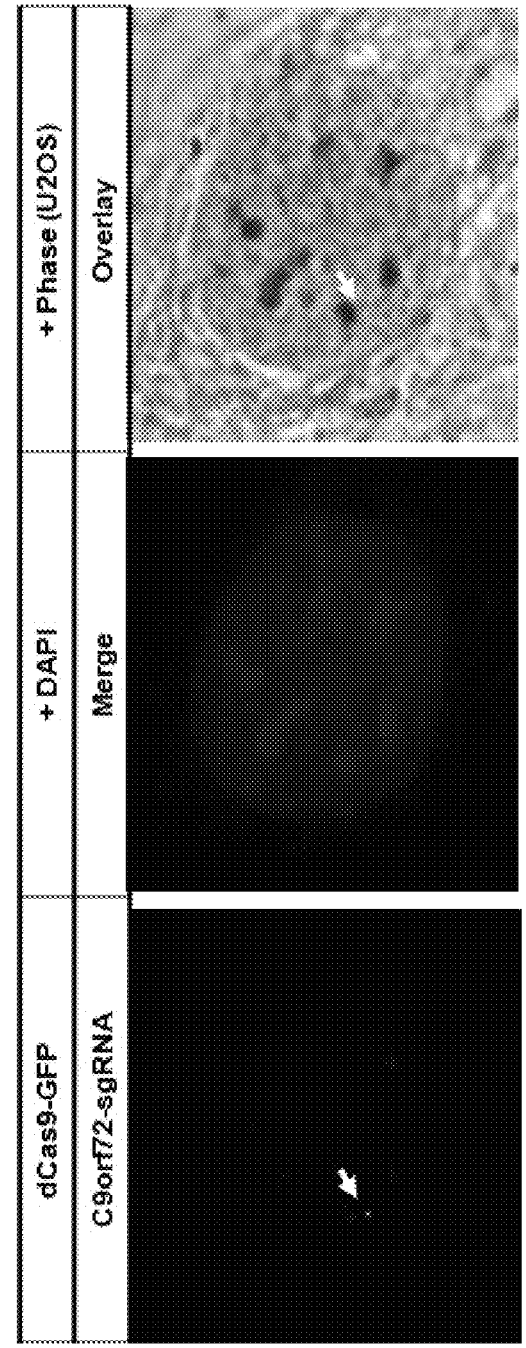
FIG. 5B: Fluorescence photomicroscopy visualization of methanol-fixed ALS fibroblast cells with dCas9-GFP and a GGGGCC-targeted (SEQ ID NO: 1) sgRNA that resulted in a single focal site (arrow). This means that the non-expanded wild-type allele has an insufficient number of repeats to be detected. Indeed no fluorescent spot was observed in control cells without the expansion (not shown).

The presently disclosed compositions were then employed with a fibroblast cell line derived from a patient with the neurodegenerative disease amyotrophic lateral sclerosis (ALS). In this patient's form of ALS, one of two alleles of a c9orf72 gene contains a very long expansion sequence in its first intron comprising greater than 1000 repeats of a hexanucleotide GGGGCC (SEQ ID NO: 1). Consequently, a dCas9-GFP and a sgRNA were designed to target a GGGGCC (SEQ ID NO: 1) hexanucleotide repeat in the first intron of the C9orf72 locus. See, FIG. 5A. Incubation of methanol-fixed ALS fibroblast cells with dCas9-GFP and a GGGGCC- (SEQ ID NO: 1) targeted sgRNA resulted in a single focal site (e.g., representing a single fluorescent signal). See, FIG. 5B; arrow. In one embodiment, the sgRNA is an sgRNA-W1 having a sequence of 5'-GCC-GGGGCC-GGGGCC-GGGGC-3' (SEQ ID NO: 3). In one embodiment, the sgRNA is an sgRNA-C1 having a sequence of 3'-CCCGG-CCCCGG-CCCCGG-GGG-5' (SEQ ID NO: 4). Although it is not necessary to understand the mechanism of an invention, it is believed that since only one signal is observed means that a non-expanded wild-type allele has an insufficient number of repeats to be detected. Normally, any sensitivity limitation with an analytical method is problematic but in the presently disclosed dCas9 method sensitivity limits constitute an advantage, in that a clinically-meaningful expanded allele is readily detectable. Thus, the data suggests that a detected single signal represents a mutated allele and demonstrate that the method disclosed herein can detect a C9orf72 sequence repeat expansion in patient cells.

B. Sensitivity and Specificity of the CARDS Assay

Although it is not necessary to understand the mechanism of an invention, it is believed that many different variables contribute to achieving optimal results, defined as robust signal detection in >10% of diseased patient cells and ~0% in non-diseased subject control cells. For example, data determined when using various molar ratio mixtures of sgRNA:dCas9 (1:1, 2:1, 4:1, etc.) can be contrasted and compared. Then different concentrations of the optimal ratio mixture can be applied to cells such the percentage of positive cells at each amount is determined. A percentage versus concentration plot of the mixture can be constructed to obtain a dose response curve. By examining the curve in both patient and control cells, a concentration can be determined at which robust signals can be detected in patient cells but no signal in control cells. Then, the presently disclosed method can reliably distinguish between diseased cells (e.g. for example, C9orf72 fibroblast cells derived from ALS patients) and non-diseased control cell lines. Preliminary data demonstrated ~1% positive cells in a C9orf72 patient line having 1200 expansion repeats and no positive cells in a control line. Nonetheless, it is contemplated that the present method identifies a positive rate in >10% patient cells and none in control cells.

In other embodiments, the present invention contemplates a fusion dCas9 protein comprising a plurality of GFP proteins, wherein said GFP proteins are attached together with flexible linkers. In one embodiment, the plurality of GFP proteins comprises three GFP proteins. Using such a fusion dCas9 protein with either one or multiple GFPs has the advantage of completing the procedure in a single step. See, FIG. 4 and FIG. 5.

Figure 6:
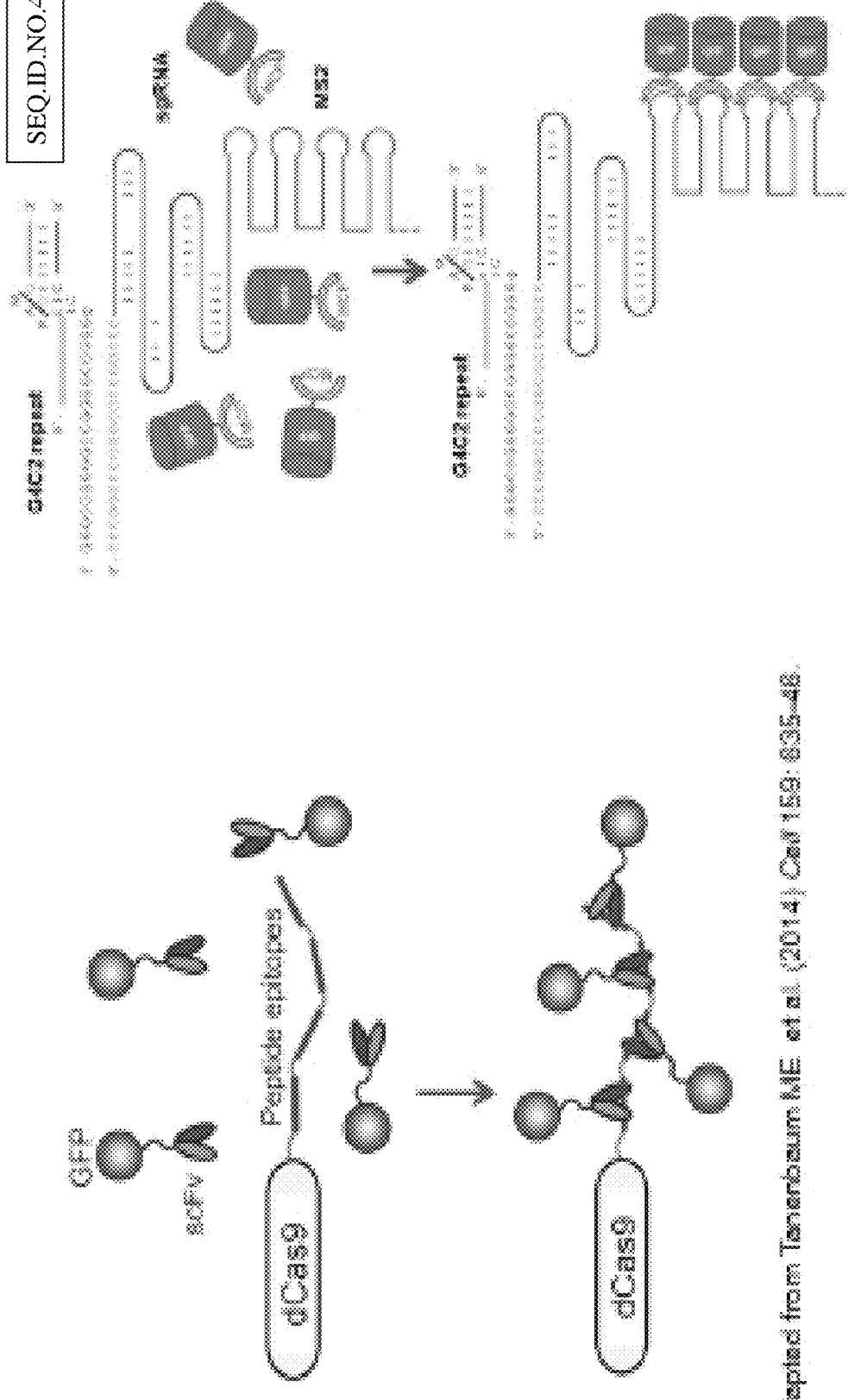
FIG. 6 illustrates alternative CARDS strategies for enhancing expansion repeat sequence detection. Left panel: dCas9 is fused with an array of peptides that are epitopes for a single chain variable fragment (scFv) attached to a GFP-decorated bead, resulting in signal amplification. Right panel: The designed single guide RNA (red and blue) has at its 3' end up to 24 binding sites (green loops) for the phage MS2 coat protein (MCP) tagged with GFP, adding additional signal amplification at the CRISPR-targeted chromosomal labeling site.

In one embodiment, the present invention contemplates a fusion dCas9 protein comprising a plurality of peptide epitopes. In one embodiment, the fusion dCas9 protein comprises a 24×SunTag epitope. In one embodiment, the 24×SunTag epitope has specific affinity for a single chain variable fragment-GFP fusion protein (scFv-GFP). After a fusion dCas9-epitope peptide and sgRNA are applied to the cells, excess dCas9-peptide/sgRNA complex is washed off. The cells may then be incubated with a scFv-GFP. The scFv-GFP binds to the peptides, bringing numerous GFP molecules to the repeat expansion site and amplifying the signal. See, FIG. 6, left panel.

In one embodiment, the present invention contemplates a sgRNA sequence comprising a plurality of RNA binding sites. In one embodiment, the sgRNA comprises up to twenty-four RNA binding sites (e.g., a 24×MS2 epitope). In one embodiment, the RNA binding site has specific affinity for a phage MS2 coat protein (MCP) tagged with GFP. After a dCas9 protein and sgRNA-24×MS2 are applied to the cells, excess dCas9/sgRNA complex may be washed off. Then the cells are incubated with MS2-GFP fusion proteins. The MS-GFP binds to the MS2 RNA motifs, bringing numerous GFP molecules to the repeat expansion site and amplifying the signal. See, FIG. 6, right panel; Bertrand et al., (1998) Localization of ASH1 mRNA particles in living yeast. Mol Cell 2:437-445; and Tanenbaum et al., (2015) A protein-tagging system for signal amplification in gene expression and fluorescence imaging. Cell 159:635-646.

C. Diagnostic Clinical Compositions

In one embodiment, the present invention contemplates a composition comprising a dCas9 protein, an sgRNA sequence that is complementary to at least a portion of a DNA expansion repeat sequence and a CARDS buffer. Although it is not necessary to understand the mechanism of an invention, it is believed that the dCas9 protein and sgRNA sequences are produced by in vitro translation and transcription.

In one embodiment, the present invention contemplates a composition comprising a pre-formed dCas9:sgRNA complex and a CARDS buffer. Based upon present knowledge of CRISPR biochemistry (i.e., for example, an equilibrium association constant of the Cas9:sgRNA complex) a dCas9 protein and sgRNA expansion repeat targeted sequences can be pre-assembled in vitro into a complex and then applied to the test cells.

V. Kits

In one embodiment, the present invention contemplates a reagent kit for diagnosis of any DNA repeat expansion-based human, animal (veterinary) or plant (agriculture, horticulture, sylviculture) disease or condition. In one embodiment, the kit provides diagnosis of at least twenty-four (24 human) neuromuscular diseases. The kits described herein also comprise reagents for performing extracting DNA from blood cells and detecting the expansion using PCR or Southern blots.

In one embodiment, the present invention contemplates a reagent kit comprising a dCas9 protein and at least one DNA repeat expansion sequence-targeted sgRNA. With the provided instructions, data can be obtained from a biological sample including, but not limited to, a blood sample or a buccal mucosal cell smear sample and completed in less than an hour.

In one embodiment, the present invention contemplates a kit comprising: a) a first container comprising a labeled nuclease-dead Cas9 (dCas) protein; b) a second container comprising a single guide ribonucleic acid (sgRNA) sequence that is complementary to at least a portion of a deoxyribonucleic acid repeat expansion sequence; c) a buffer that is compatible with said dCas9 protein and said sgRNA; and d) a sheet of instructions for detecting a deoxyribonucleic acid repeat expansion sequence associate with a genetic disease. In one embodiment, the deoxyribonucleic acid repeat expansion sequence is associated with a genetic disease. In one embodiment, the genetic disease comprises a mutated c9orf72 gene. In one embodiment, the mutated c9orf72 gene results in amyotrophic lateral sclerosis. In one embodiment, the sgRNA sequence comprises a plurality of core repeat sequences. In one embodiment, the plurality of core repeat sequences comprises GGGGCC (SEQ ID NO: 1). In one embodiment, the plurality of core repeat sequences comprises CCCCGG (SEQ ID NO: 2). In one embodiment, the sgRNA is an sgRNA-W1 having a sequence of 5'-GCC-GGGGCC-GGGGCC-GGGGC-3' (SEQ ID NO: 3). In one embodiment, the sgRNA is an sgRNA-C1 having a sequence of 3'-CCCGG-CCCCGG-CCCCGG-GGG-5' (SEQ ID NO: 4). In one embodiment, the label is a green fluorescent protein.

In one embodiment, the kit can include one or more containers comprising a vector coding for a nuclease-deficient Cas9 (dCas9) DNA vector comprising an sgRNA targeting sequence fused with a nucleic acid sequence encoding a fluorescent protein. In one container, the fluorescent protein may include, but is not limited to, a green fluorescent protein, a red fluorescent protein, or a blue fluorescent protein.

The kit can optionally include enzymes capable of performing PCR (i.e., for example, DNA polymerase, Taq polymerase and/or restriction enzymes). The kit can optionally include a delivery vehicle for said vectors (e.g., a liposome). The reagents may be provided suspended in the excipient and/or delivery vehicle or may be provided as a separate component which can be later combined with the excipient and/or delivery vehicle. The kit may optionally contain additional therapeutics to be co-administered with the vectors to affect the desired transcriptional regulation.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in affecting transcriptional regulation of cell cultures and delivery of said vectors to said cell cultures. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

The following examples are provided in order to demonstrate and further illustrate certain preferred embodiments and aspects of the present invention and are not to be construed as limiting the scope thereof.

Example 1

Construction of Cas9 Expression Plasmids

Human-codon optimized dCas9 (nuclease-dead) from *S. pyogenes* (18), *N. meningitidis* and *S. thermophilus* (15) were fused to 1XGFP, 2XGFP, 3XGFP, 3XmCherry or 3XTagBFP and subcloned into pHAGE-DEST lentiviral vector. Esvelt K M, et al. Orthogonal Cas9 proteins for RNA-guided gene regulation and editing. *Nat. Methods* 10(11): 1116-1121; and Kearns N A, et al. (2014) Cas9 effector-mediated regulation of transcription and differentiation in human pluripotent stem cells. Development 141 (1):219-223.

To optimize the promoters for U2OS and RPE1 cells, the EF1α promoter in the pHAGE-EFla-DEST vector was replaced by EFS, SFFV and CMV-TetO promoters respectively and results in the pHAGE-EFS-DEST, pHAGE-SFFV-DEST and pHAGE-TO-DEST. To optimize the nuclear localization, 2× SV40 NLSs were fused to *S. pyogenes* dCas9, *N. meningitidis* dCas9, while up to 6×SV40 NLSs were fused to *S. thermophilus* dCas9. A list of Cas9 labeled fusion proteins constructed is shown in Table 3.

TABLE 3

Exemplary Cas9 Labeled Fusion Proteins

|   | Promoter | dCas9 Fusion protein | NLS |
|---|---|---|---|
| 1 | EF1 α | NLS-Sp dCas9-NLS-sfGFP | 2X |
| 2 | SSFV | NLS-Sp dCas9-NLS-sfGFP | 2X |
| 3 | EFS | NLS-Sp dCas9-NLS-sfGFP | 2X |
| 4 | CMV-TetO | NLS-Sp dCas9-NLS-sfGFP | 2X |
| 5 | CMV-TetO | NLS-Sp dCas9-NLS-2XsfGFP | 2X |
| 6 | CMV-TetO | NLS-Sp dCas9-NLS-3XsfGFP | 2X |
| 7 | CMV-TetO | NLS-Sp dCas9-NLS-3XmCherry | 2X |
| 8 | CMV-TetO | NLS-Nm dCas9-NLS-3XsfGFP | 2X |
| 9 | CMV-TetO | NLS-Nm dCas9-NLS-3XmCherry | 2X |
| 10 | CMV-TetO | NLS-St1 dCas9-NLS-3XsfGFP | 2X |
| 11 | CMV-TetO | NLS-St1 dCas9-2XNLS-3XsfGFP | 3X |
| 12 | CMV-TetO | NLS-St1 dCas9-3XNLS-3XsfGFP | 4X |
| 13 | CMV-TetO | NLS-St1 dCas9-3XNLS-3XTagBFP2 | 4X |
| 14 | CMV-TetO | NLS-St1 dCas9-3XNLS-3XsfGFP-NLS | 5X |
| 15 | CMV-TetO | NLS-St1 dCas9-3XNLS-3XsfGFP-2XNLS | 6X |

Example 2

Construction of sgRNA Expression Vectors

The sgRNA expression vector is based on the pLKO.1 lentiviral expression plasmid containing CcdB gene between two BbsI sites for inserting guide sequences into the sgRNAs. Optimized sgRNA for *S. pyogenes* Cas9 was subcloned into pLKO.1-Hygro, resulting in pLH-Sp sgRNA2. Nm sgRNA mutants for *N. meningitidis* Cas9 were subcloned into pLKO.1-Hygro, resulting in pLH-Nm sgRNAm1 and pLHNm sgRNA1.1. St1 sgRNA mutants for *S. thermophilus* Cas9 were subcloned into pLKO.1-Hygro, resulting in pLH-St1 sgRNAm1, pLH-St1 sgRNAm7, pLHSt1 sgRNA1.1, pLH-St1 sgRNA2.1 and pLH-St1 sgRNA3.1. A rapid guide RNA expression plasmids construction protocol was optimized as follows: a pair of oligos (2 µM) were denaturing at 95° C. for 3 min and cooling down to room temperature, and the mixture of oligos (4 nM) and sgRNA vectors (100 ng) were quickly digested by BbsI and ligated by T7 ligase at 37° C. for 10 min in the same tubes, and then directly subjected to transformation using CcdB as counter-selection. The sgRNA vectors and guide RNA sequences are listed in Tables 4 and 5 respectively.

TABLE 4

Exemplary sgRNA Vectors

| | Vector Name | sgRNA expression vector Cassette |
|---|---|---|
| 1 | pLH-Sp sgRNA2 | U6 promoter-BbsI-CcdB-BbsI-Sp sgRNA2 |
| 2 | pLH-Nm sgRNAm3 | U6 promoter-BbsI-CcdB-BbsI-Nm sgRNAm3 |

TABLE 4-continued

Exemplary sgRNA Vectors

| | Vector Name | sgRNA expression vector Cassette |
|---|---|---|
| 3 | pLH-Nm sgRNA1.1 | U6 promoter-BbsI-CcdB-BbsI-Nm sgRNA1.1 |
| 4 | pLH-St1 sgRNAm1 | U6 promoter-BbsI-CcdB-BbsI-St1 sgRNAm1 |
| 5 | pLH-St1 sgRNAm7 | U6 promoter-BbsI-CcdB-BbsI-St1 sgRNAm7 |
| 6 | pLH-St1 sgRNA1.1 | U6 promoter-BbsI-CcdB-BbsI-St1 sgRNA1.1 |
| 7 | pLH-St1 sgRNA2.1 | U6 promoter-BbsI-CcdB-BbsI-St1 sgRNA2.1 |
| 8 | pLH-St1 sgRNA3.1 | U6 promoter-BbsI-CcdB-BbsI-St1 sgRNA\3.1 |

TABLE 5

Exemplary sgRNA Sequences, Targets And PAMs

| | dCas9 | Target | Guide RNA sequence | SEQ ID NO: | PAM |
|---|---|---|---|---|---|
| 1 | S. pyogenes | DMC4 | GTGGCGTGACCTGTGGATGCTG | 17 | GG |
| 2 | S. pyogenes | Telo-TA | GGTTAGGGTTAGGGTTAGGG | 18 | TA |
| 3 | S. pyogenes | Telo-GT | AGGGTTAGGGTTAGGGTTAG | 19 | GT |
| 4 | S. pyogenes | Telo-AG | GTTAGGGTTAGGGTTAGGGT | 20 | AG |
| 5 | S. pyogenes | Sp-Telo | TTAGGGTTAGGGTTAGGGTT | 21 | GG |
| 6 | S. pyogenes | Telo-17 | GGGTTAGGGTTAGGGTT | 22 | GG |
| 7 | S. pyogenes | Telo-13 | TAGGGTTAGGGTT | 23 | GG |
| 8 | S. pyogenes | Telo-10 | GTTAGGGTT | 24 | GG |
| 9 | S. pyogenes | Telo-06 | AGGGTT | 25 | GG |
| 10 | S. pyogenes | C9-1 | TGGAATGGAATGGAATGGAA | 26 | GG |
| 11 | S. pyogenes | C9-2 | TGTCTGTGAGGAAGCTCCCC | 27 | GG |
| 12 | S. pyogenes | C13-1 | TAAGCATGGACCATTCCTTC | 28 | GG |
| 13 | S. Pyogenes | C13-2 | GGGCCAGGACCTCTAAAA | 29 | GG |
| | | | CCGGGGAAGTGCTGAGTC | 30 | GG |
| | | | TGGTGGGTGTAGACACGG | 31 | GG |
| 14 | N. meningitidis | Telo-AGGG | GGTTAGGGTTAGGGTTAGGGTTAG | 32 | AGGG |
| 15 | N. meningitidis | Telo-GGGT | GTTAGGGTTAGGGTTAGGGTTAGG | 33 | GGGT |
| 16 | N. meningitidis | Nm-Telo | TTAGGGTTAGGGTTAGGGTTAGGG | 34 | GGTT |
| 17 | N. meningitidis | Telo-GTTA | TAGGGTTAGGGTTAGGGTTAGGGT | 35 | GTTA |
| 18 | N. meningitidis | C13-1 | CTCCATCCTGAAGGAATGGTCCAT | 36 | GCTT |
| 19 | S. thermophilus | St1-Telo | GGTTAGGGTTAGGGTTAGGG | 37 | AGGG |
| 20 | S. thermophilus | C9-1 | ATGGAATGGAATGGAATGGA | 38 | GGAA |

Example 3

Cell Culture and Transfection

U2OS cells were cultured at 37° C. in Dulbecco-modified Eagle's Minimum Essential Medium (DMEM; Life Technologies) supplemented with 10% (vol/vol) FBS. RPE1 cells were cultured at 37° C. in DMEM:F12 medium supplemented with 10% (vol/vol) FBS. For live imaging, cells were grown on 35 mm glass bottom dishes (MatTek). In experiments with U2OS cells, a total of 150 ng dCas9 and 750 ng sgRNAs plasmid were cotransfected into 35 mm glass bottom dishes using Lipofectamine 2000 (Life Technologies) and the cells were incubated for another 48 hours. For RPE1 cells, a total of 50 ng dCas9 and 250 ng sgRNAs plasmids were co-transfected into 35 mm glass bottom dishes using Lipofectamine LTX (Life Technologies).

Example 4

Fluorescence Microscopy

The microscope stage incubation chamber was maintained at 37° C. (19) and phase-contrast and fluorescence microscopy was performed as described previously. Jacobson M R, Pederson T (1997) RNA traffic and localization reported by fluorescence cytochemistry. Analysis of mRNA Formation and Function, ed Richter J D (Academic, New York), pp 341-359; and Ma H, Reyes-Gutierrez P, Pederson T (2013) Visualization of repetitive DNA sequences in human chromosomes with transcription activator-like effectors. Proc Natl Acad Sci USA 110(52):21048-21053. mCherry was excited at 556/20 nm (wavelength/bandwidth) and its emission was collected in a 630/91 nm channel. sfGFP was excited at 470/28 nm and its emission was collected in a 512/23 nm channel; TagBFP was excited at 387/11 nm and its emission collected using a 464/23 nm filter. Imaging data were acquired and analyzed by Meta-Morph acquisition software (Molecular Devices).

Example 5

Mining for Chromosome-Specific Repeats

The human reference genome hg19 was downloaded from the UCSC genome browser (genome.ucsc.edu). The gaps (regions labeled with N's) in chromosomes 9 and 13 were replaced with randomly generated nucleotides. The bioinformatics tool Tandem Repeat Finder was used to identify tandem repeats in chromosomes 9 and 13. Benson G (1999) Tandem repeats finder: a program to analyze DNA sequences. *Nucleic Acids Res.* 27(2):573-580.

Highly conserved repeats with copy numbers >100 were selected as candidates for CRISPR labeling. 23-mers in the tandem repeats ending with GG were used for design of Sp sgRNAs for C9-1, C9-2, C13-1, C13-2. 28-mers ending with GCTT were used for design of Nm sgRNAs for C13-1 and 26-mers ending with GGAA were used for design of St1 sgRNA for C9-1.

The detailed parameters for each targeted repeats are as follows. C9-2 is located in a subtelomeric region q34.3 of chr 9 with the location chr9: 140459676-140463065 and contains 115 copies of sgRNA target sites. C13-1 consists of 177 copies of sgRNA target sites, located in the subtelomeric region q34 of chr 13 with the location chr 13: 112930173-112968847. C13-2 consists of three neighboring tandem repeats in q34 of chr 13 chosen to achieve a combined 102 copies of sgRNA target sites with the following locations: chr13: 114793685-114795158 with 22 copies of target sites; chr13: 114848979-114852850 with 57 copies of target sites; chr13: 114903631-114905572 with 23 copies of target sites.

A BLAST alignment tool was used to verify the chromosome specificity of these sgRNA target sites in human genome Kent W J (2002) BLAT-the blast-like alignment tool. Genome Res. 12(4):656-664.

C9-1 was a tandem array of GGAAT repeats, which are highly concentrated in the pericentromeric region of chr 9. Eymery A, Souchier C, Vourc'h C, Jolly C. (2010) Heat shock factor 1 binds to and transcribes satellite II and III sequences at several pericentromeric regions in heat-shocked cells. Exp Cell Res 316(11):1845-1855.

Example 6

Guide RNA Stability In Live Human Cells

Figure 17:
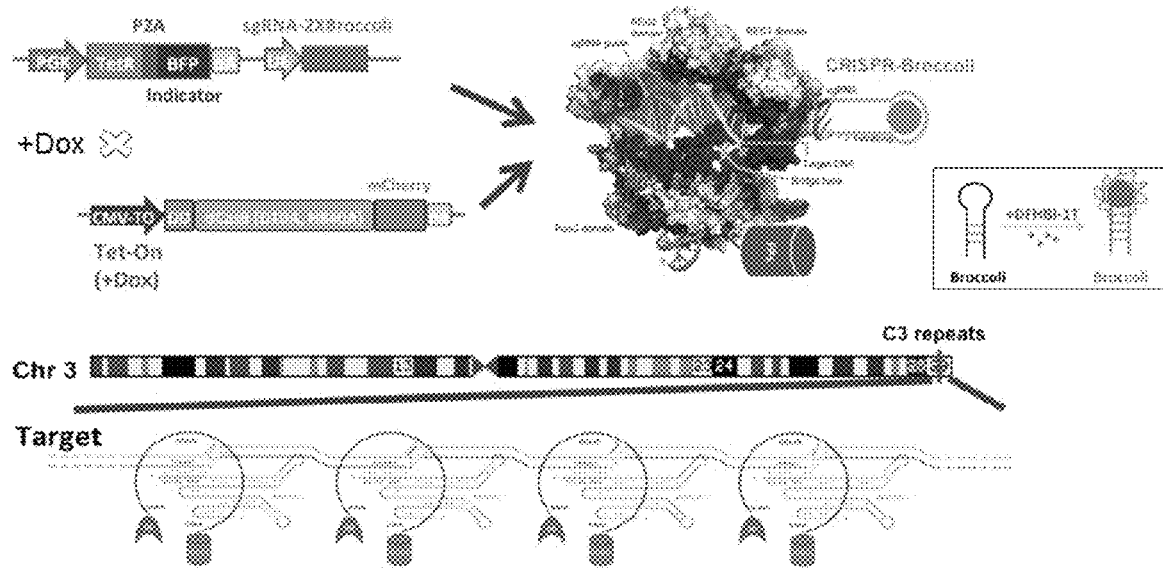
FIG. 17 presents one embodiment of a TetR doxycycline inducible sgRNA construct using CRISPRainbow dCAS9 constructs, referred to herein as, "Broccoli", and one embodiment of a conventional mCherry-DD dCAS9 construct whose activity is blocked by Shield 1.
Figure 17:
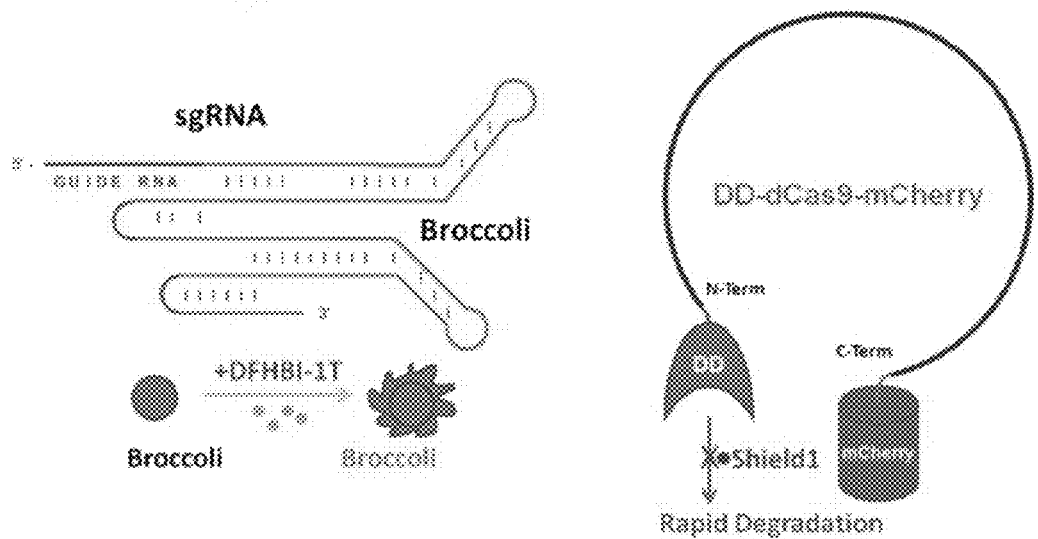
Figure 18:
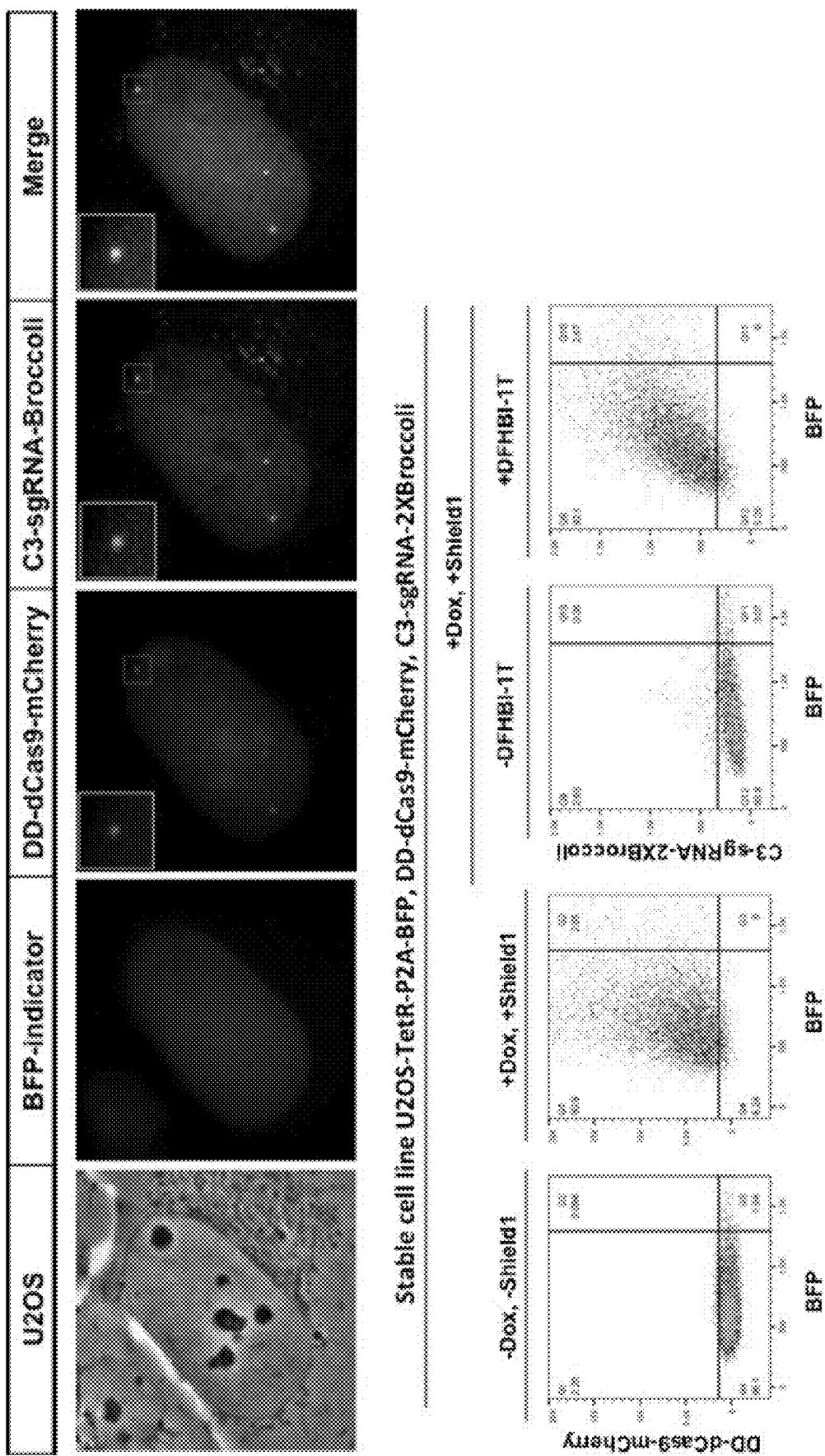
FIG. 18 presents exemplary data showing TetR doxycycline inducible sgRNA construct stability in U2OS cells.
Figure 19:
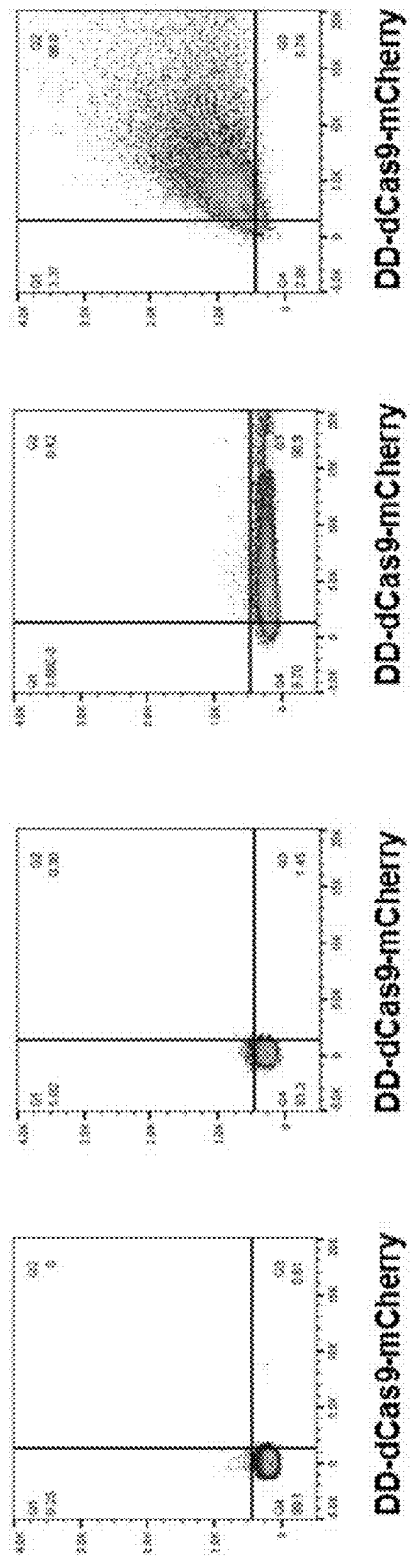
FIG. 19 presents exemplary data showing the effect of the presence or absence of dCAS9 on sgRNA stability in U2OS cells.
Figure 20:
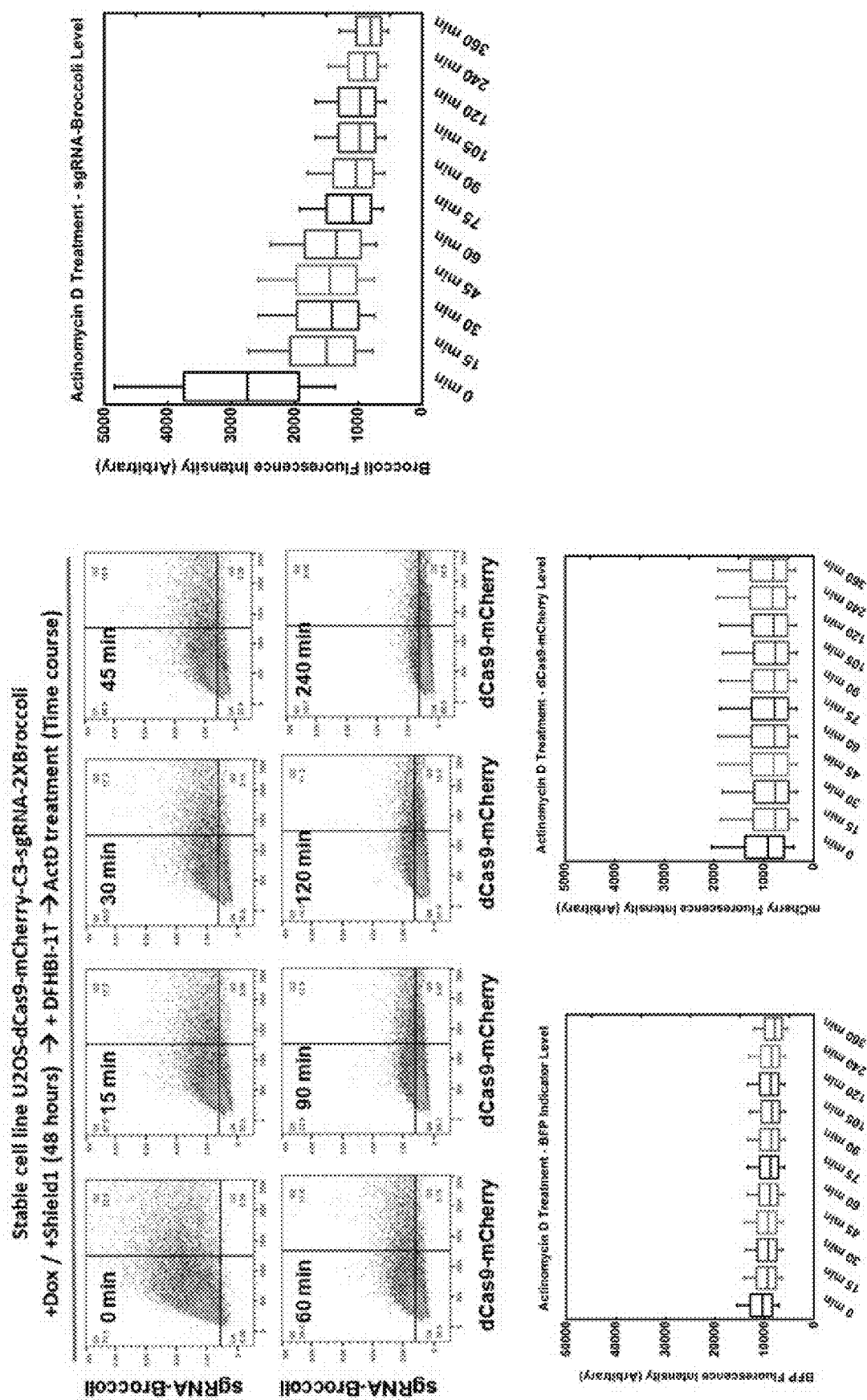
FIG. 20 presents exemplary data showing the effect of actinomycin D on sgRNA stability in TetR doxycycline inducible CRISPRainbow constructs.

The data presented herein evaluates the existence of guide RNAs in live cells by using fluorescence microscopy. A TetR-doxycycline inducible sgRNA construct was designed and created to evaluate the lifetime and stability of sgRNAs in living systems. FIG. 17. The U20S cell line was used to evaluate the stability of these various constructs. FIG. 18. The effect of the presence or absence of the dCAS9 protein was then evaluated. FIG. 19. The effect of actinomycin D was further evaluated on sgRNA stability using the TetR doxycycline inducible dCAS9 constructs. FIG. 20.

In live cells, sgRNA is extremely unstable without Cas9. The half-live of dCas9/sgRNA complexes is within 15 minutes. sgRNA/Cas9 assembly and stability determines sgRNA level. Poor assembly of sgRNA/Cas9 complexes can result from defective sgRNAs (e.g. short target sequence) or Cas9 (e.g. Cas9 mutant). Steady-state sgRNA level is a limiting factor for efficient DNA targeting. sgRNA/Cas9/DNA complexes are dynamic and the stability depends on sgRNA length.

Example 7

CRISPR/Cas9 Target Binding Efficiency

Figure 21:
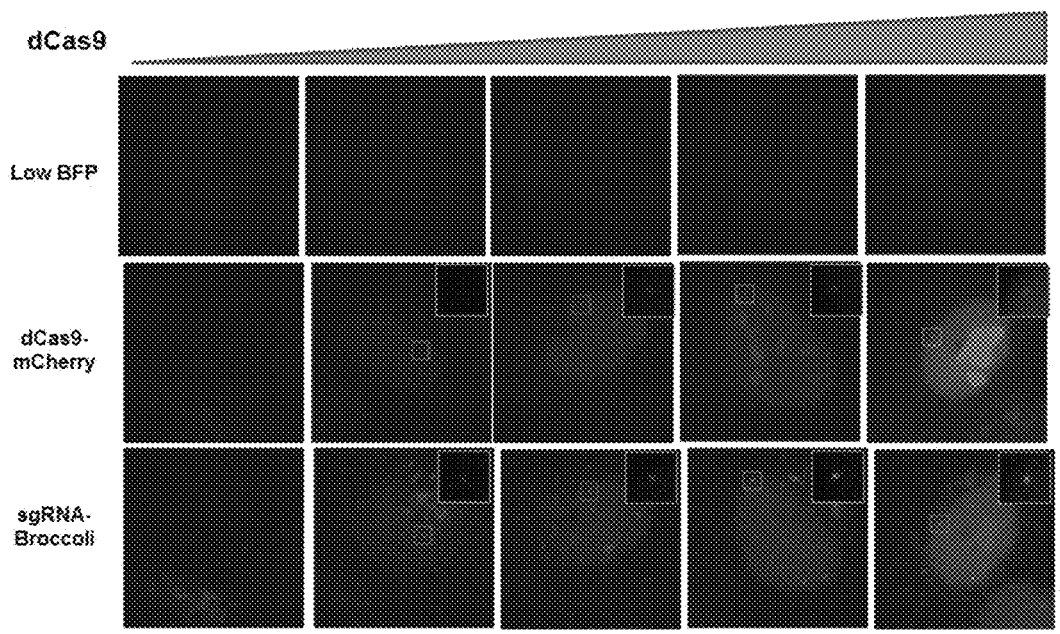
FIG. 21 presents exemplary data showing the on-target efficiency of a CRISPRainbow "Broccoli" construct as compared to a conventional mCherry-dCAS9 label at various low intensity blue fluorescent protein (BFP) background levels.
Figure 22A:
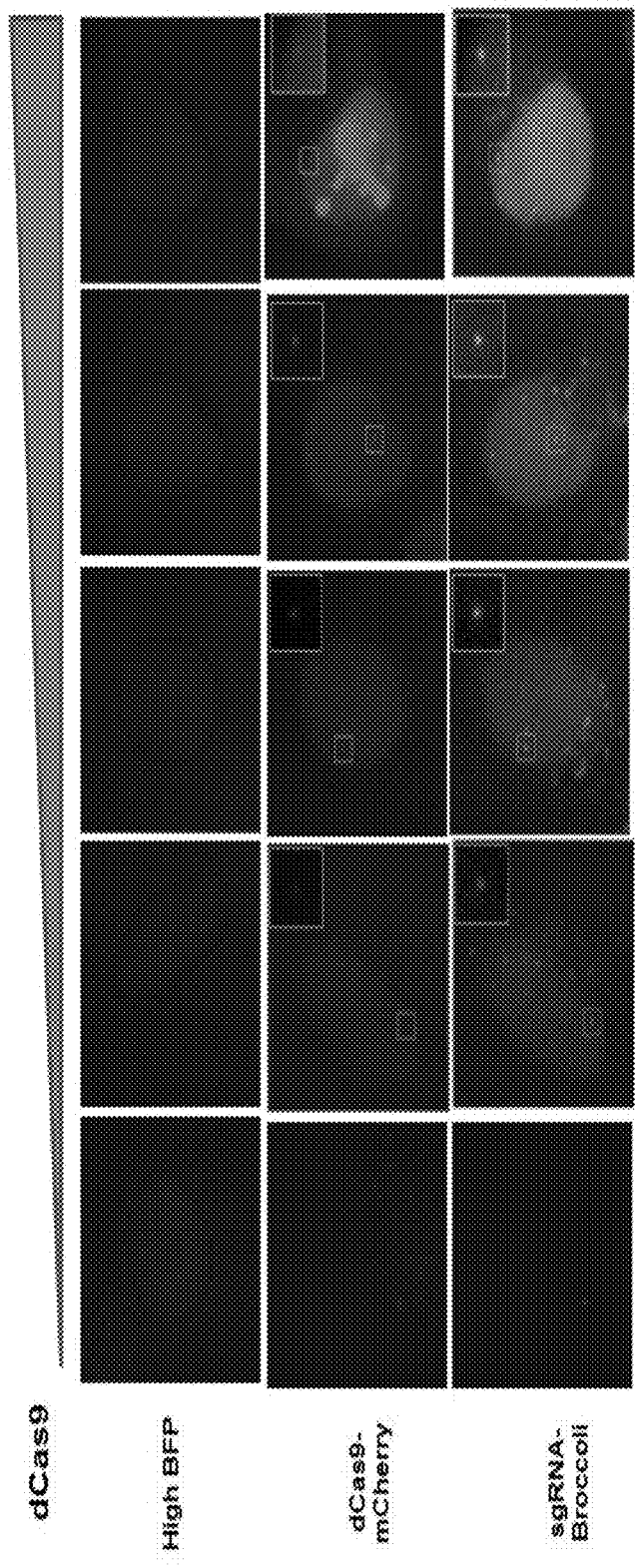
FIG. 22A presents exemplary data showing the on-target efficiency of a CRISPRainbow "Broccoli" construct as compared to a conventional mCherry-dCAS9 label at various high intensity blue fluorescent protein (BFP) background levels.
Figure 22B:
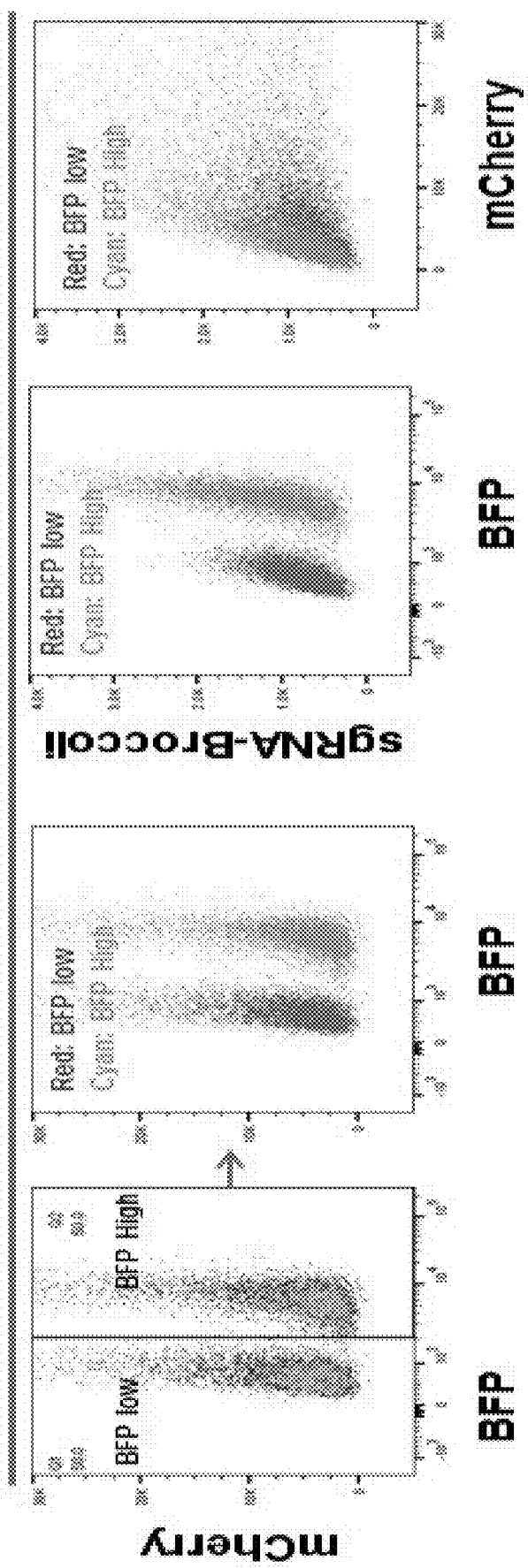
FIG. 22B presents a comparative analysis between the data on-target efficiencies presented in FIG. 21 and FIG. 22A.
Figure 23:
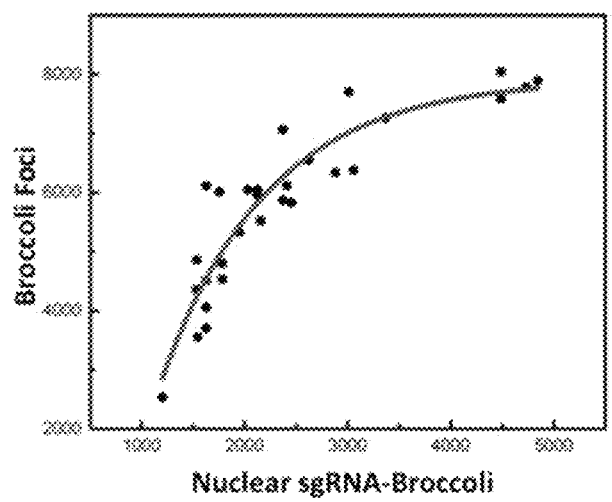
FIG. 23 presents exemplary data showing the effect of dCAS9 concentration on the efficiency of sgRNA on-target intensity.
Figure 24:
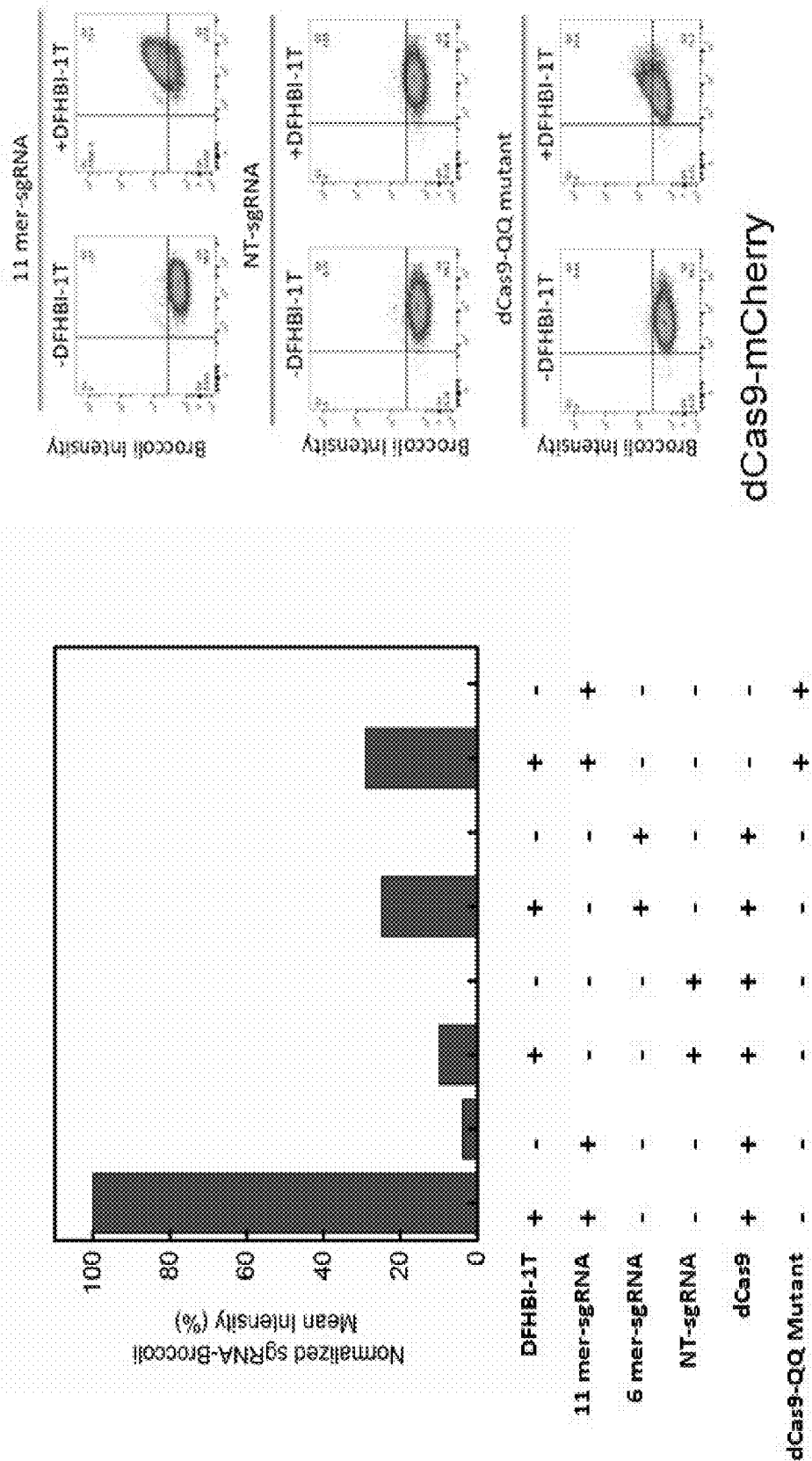
FIG. 24 presents exemplary data showing a complete analysis of the different factors believed to play a role in sgRNA on-target intensity efficiency.

The data presented herein evaluated the efficiency of CRISPR/Cas9 target binding using the Broccoli CRISP-Rainbow construct as compared to an mCherry DD dCAS9 construct and low intensity and high intensity blue fluorescent protein background levels. FIG. 21 and FIG. 22, respectively. The data showed that the concentration of dCAS9 relative to the sgRNA played a role in determining sgRNA stability. FIG. 23. Further, a complete assessment of other factors believed to play a role in sgRNA on-target intensity efficiency was evaluated. FIG. 24.

Example 8

Effect of Nucleotide Mismatch on sgRNA On-Target Residence Time

Figure 25:
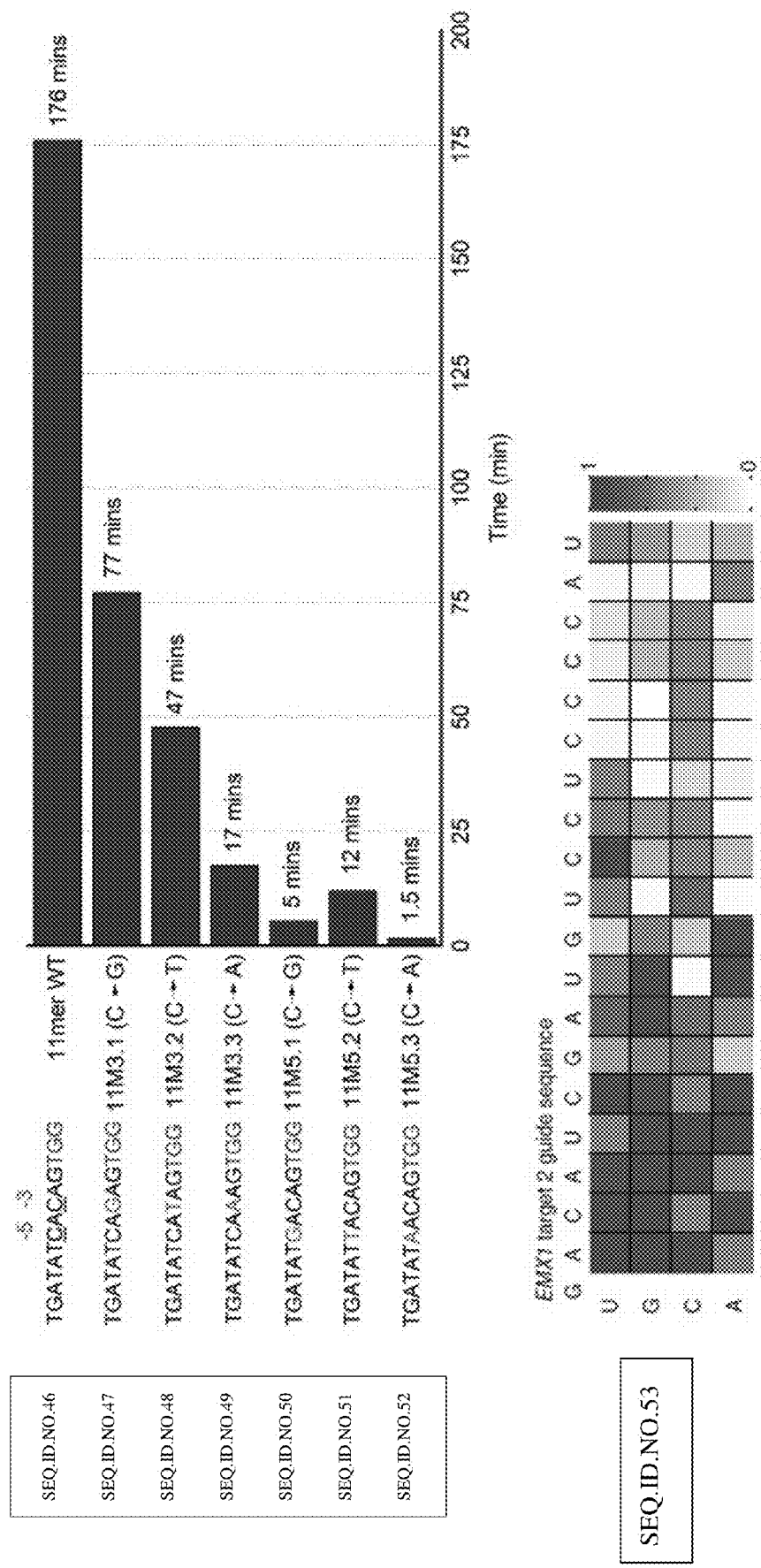
FIG. 25 presents exemplary data showing the effect of sgRNA mutations on sgRNA on-target residence time.
Figure 26:
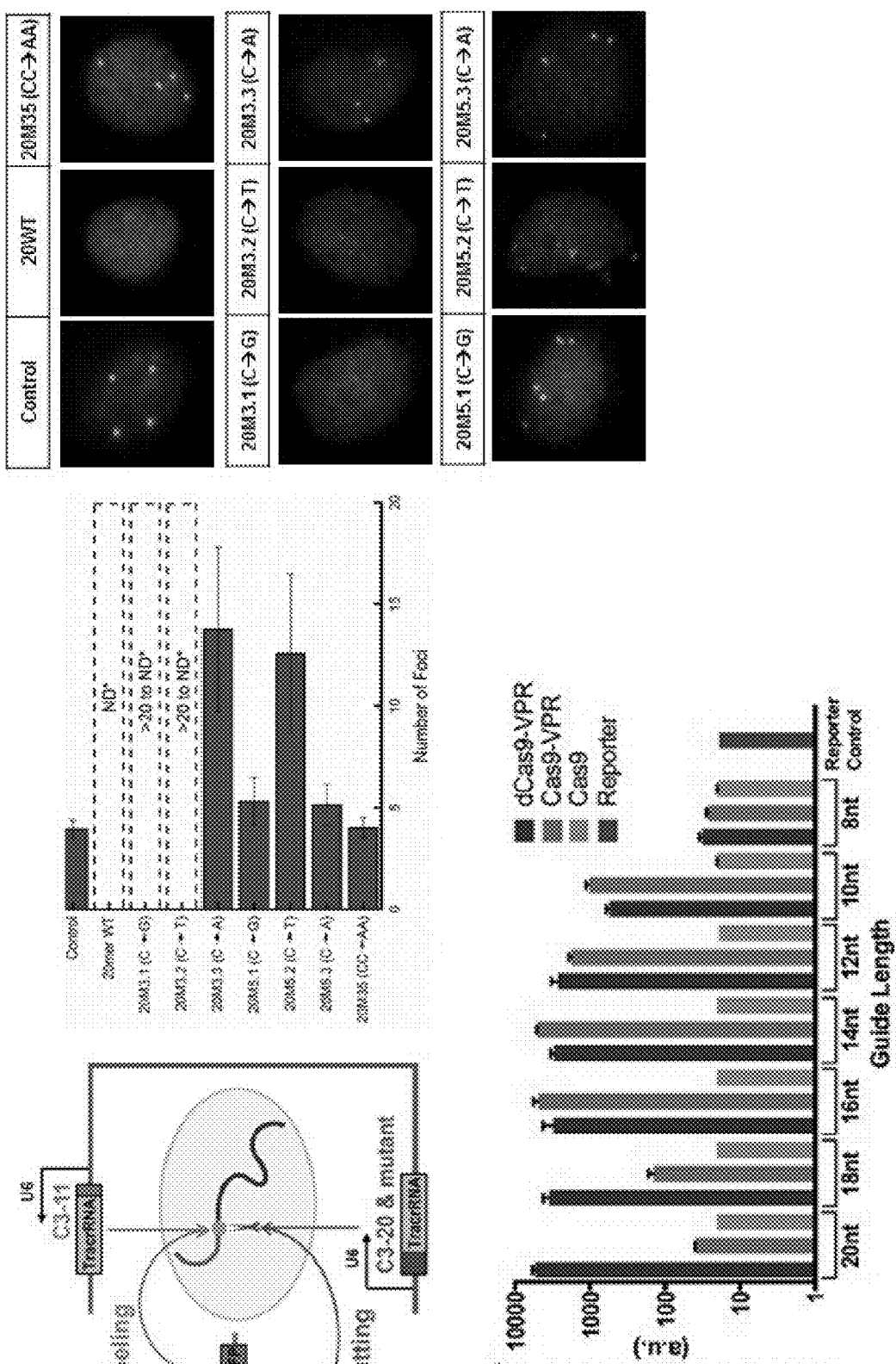
FIG. 26 presents exemplary data showing the effect of sgRNA nucleotide mismatches on CAS9 cleavage efficiency.

The impact of various mutations in the sgRNA sequences was evaluated for their ability to affect stable hybridization to a specific gene target loci. Hsu et al., *Nat. Biotechnol.* 31:827-32 (2013); and FIG. 25. Further, the effect of how sgRNA nucleotide mismatches effect CAS9 cleavage efficiency was determined in live cells. Kiani et al, *Nat Methods*

Example 9

Telomeric Repeat Sequence Detection Using Self-Labeling Fluorescent Tags

In this example, telomere and C9orf72 repeats were detected from patient-derived fibroblast (FTD #26) using Cas9-HaloTag-JF549 and telomere sgRNA or C9orf72 repeats sgRNA, respectively.

Figure 27:
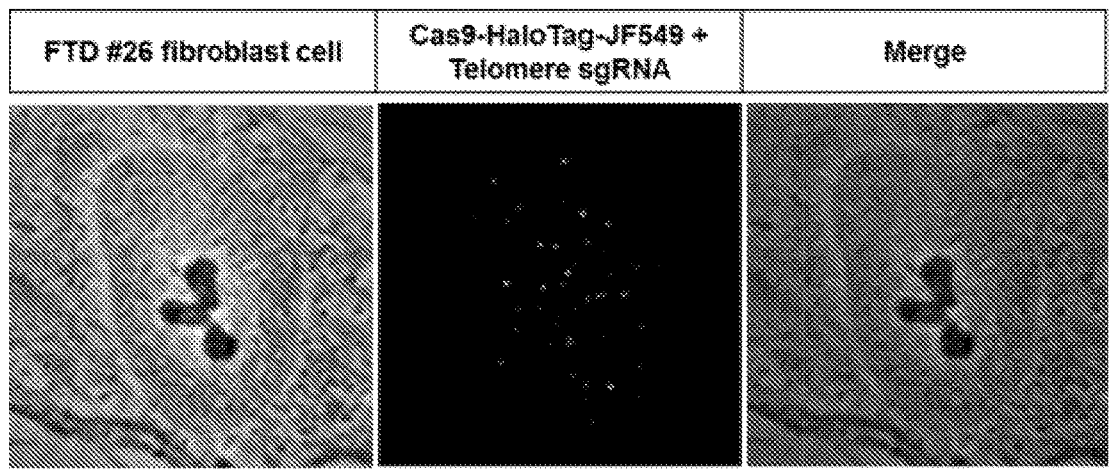
FIG. 27 presents exemplary data showing the detection of telomeric repeat sequences in a human patient.
Figure 27:
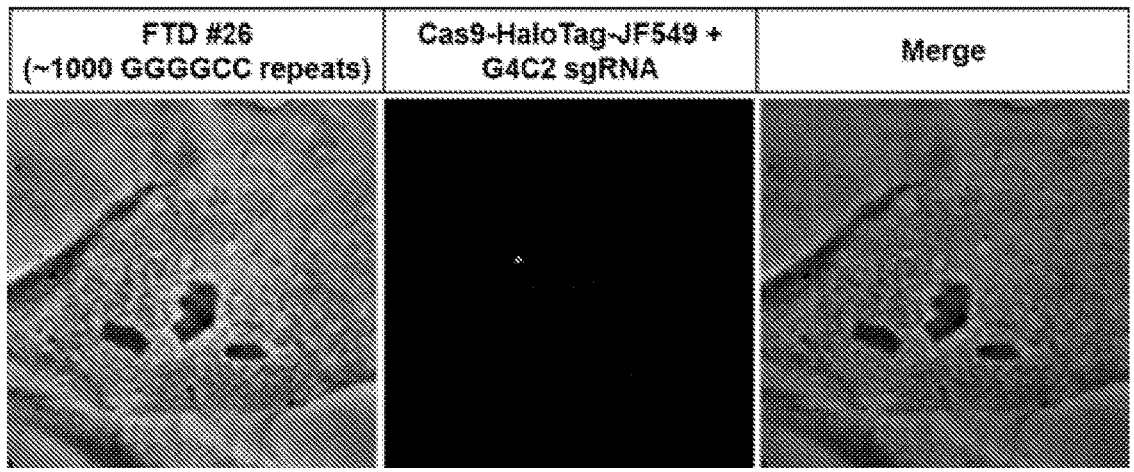

The data show a sensitive detection of the telomeres in this fibroblast cell lines which had previously been beyond conventional detection range using Cas9-GFP-based CRISPR-FISH system since the typical fibroblast telomere length are 3-10 kb. See, FIG. 27A. This FTD #26 fibroblast line was also measured to have ~1000 G4C2 repeat sequences (~6 kb) associated with an improved range of detection sensitivity using fluorescent dyes. See, FIG. 27B. The percentage of cells containing G4C2 repeats in the cell population was <5%.

The above description, and the figures to which it refers, are provided for the purpose of describing and illustrating certain preferred embodiments or examples of the invention only, and no attempt has been made to exhaustively describe all possible embodiments or examples of the invention. Thus, the following detailed description and the accompanying figures shall not be construed to limit, in any way, the scope of the claims recited in this patent application and any patent(s) issuing there from.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

We claim:

1. A composition comprising a nuclease-dead Cas9 (dCas) protein and a single guide ribonucleic acid (sgRNA) comprising at least two fluorescent proteins each bound to a different stem loop, and wherein each of said at least two fluorescent proteins have a different color.

2. The composition of claim 1, wherein said different color is selected from the group consisting of red, green and blue.

3. The composition of claim 1, wherein each of said different stem loop comprises an AU→GC mutation.

4. The composition of claim 1, wherein said different stem loop is selected from the group consisting of an MS2 stem loop, a PP7 stem loop or a boxB stem loop.

5. The composition of claim 4, wherein said M52 stem loop is bound to a MCP-blue fluorescent protein.

6. The composition of claim 4, wherein said PP7stem loop is bound to a PCP-green fluorescent protein.

7. The composition of claim 4, wherein said boxB stem loop is bound to a N22-red fluorescent protein.

8. The composition of claim 1, wherein said sgRNA sequence has three fluorescent proteins, wherein each of said three fluorescent protein are bound to a different stem loop.

9. A method for diagnosing a genetic disease, comprising:
   a) providing:
      i) a biological sample comprising a plurality of chromosomes comprising at least one gene target loci;
      ii) a composition comprising a nuclease-dead Cas9 (dCas9) protein and a single guide ribonucleic acid (sgRNA) computing at least two fluorescent proteins each bound to a different stem loop, wherein each of said at least two florescent proteins have a different color;
   b) contacting said composition with said plurality of chromosomes;
   c) forming a dCas9/sgRNA complex on said at least one gene target loci;
   d) detecting at least one color from said at least two differently corned fluorescent proteins; and
   e) identifying a repeat expansion sequence within said at least one gene target loci based upon said detected at least one color, wherein said repeat expansion sequence diagnose a genetic disease.

10. The method of claim 9, wherein said at least one gene target loci is selected from the group consisting of two gene target tac, three gene target tac, four gene target loci, five gene target loci and six gene target loci.

11. The method of claim 9, wherein used at least one color is selected from the group consisting of red, green, blue, cyan, yellow, magenta and white.

12. The method of claim 9, wherein said identifying at least two of said at least one gene target loci is simultaneous.

13. The method of claim 9, wherein said different color is selected from the group consisting of red, green and blue.

14. The method of claim 9, wherein each of said different stem loop comprises an AU→GC mutation.

15. The method of claim 9, wherein said different stem loop is selected from the soap consisting of an MS2 stem loop PP7 stem loop or a boxB stem loop.

16. The method of claim 15, wherein said MS2 stem loop is bound to a MCP-blue florescent protein.

17. The method of claim 15, wherein aid PP7 stem loop is bound to a PCP-green fluorescent protein.

18. The method of claim 15, wherein said boxB stem loop is bound to a N22-red fluorescent protein.

19. The method of claim 9, wherein said sgRNA sequence has three fluorescent proteins, wherein each of said three fluorescent proteins are bound to a different stem loop.

\* \* \* \* \*

UNITED STATES PATENT AND TRADEMARK OFFICE
CERTIFICATE OF CORRECTION

PATENT NO. : 11,390,908 B2
APPLICATION NO. : 15/757240
DATED : July 19, 2022
INVENTOR(S) : Thoru Pederson et al.

It is certified that error appears in the above-identified patent and that said Letters Patent is hereby corrected as shown below:

On the Title Page

Column 1, Item (73), Line 3-4, the co-assignee listed should read as follows:
UNIVERSITY OF CENTRAL FLORIDA RESEARCH FOUNDATION, INC.

Signed and Sealed this
Twenty-first Day of March, 2023

Katherine Kelly Vidal
Director of the United States Patent and Trademark Office

SEQUENCE LISTING

```
<160> NUMBER OF SEQ ID NOS: 53

<210> SEQ ID NO 1
<211> LENGTH: 6
<212> TYPE: DNA
<213> ORGANISM: Artificial sequence
<220> FEATURE:
<223> OTHER INFORMATION: Synthetic

<400> SEQUENCE: 1 ggggcc                                                                    6

<210> SEQ ID NO 2
<211> LENGTH: 6
<212> TYPE: DNA
<213> ORGANISM: Artificial sequence
<220> FEATURE:
<223> OTHER INFORMATION: Synthetic

<400> SEQUENCE: 2 ccccgg                                                                    6

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
gccggggccg gggccggggc                                                    20

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4 ggggccccg gccccggccc                                                     20
```

```
<210> SEQ ID NO 5
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 5 nnnngann                                                                 8

<210> SEQ ID NO 6
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 6 nnnngttn                                                                 8

<210> SEQ ID NO 7
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 7 nnnngatt                                                                 8

<210> SEQ ID NO 8
<211> LENGTH: 6
<212> TYPE: DNA
<213> ORGANISM: Artificial sequence
<220> FEATURE:
<223> OTHER INFORMATION: Synthetic

<400> SEQUENCE: 8 ttaggg                                                                   6

<210> SEQ ID NO 9
<211> LENGTH: 5
<212> TYPE: DNA
<213> ORGANISM: Artificial sequence
<220> FEATURE:
<223> OTHER INFORMATION: Synthetic

<400> SEQUENCE: 9 attcc                                                                    5
```

<210> SEQ ID NO 10
<211> LENGTH: 8
<212> TYPE: DNA
<213> ORGANISM: Neisseria meningitidis
<220> FEATURE:
<221> NAME/KEY: misc_feature
<222> LOCATION: (1)..(4)
<223> OTHER INFORMATION: n is a, c, g, or t

<400> SEQUENCE: 10 nnnngatt                                                                8

<210> SEQ ID NO 11
<211> LENGTH: 8
<212> TYPE: DNA
<213> ORGANISM: Neisseria meningitidis
<220> FEATURE:
<221> NAME/KEY: misc_feature
<222> LOCATION: (1)..(4)
<223> OTHER INFORMATION: n is a, c, g, or t

<400> SEQUENCE: 11 nnnnggtt                                                                8

<210> SEQ ID NO 12
<211> LENGTH: 7
<212> TYPE: DNA
<213> ORGANISM: Neisseria meningitidis
<220> FEATURE:
<221> NAME/KEY: misc_feature
<222> LOCATION: (1)..(3)
<223> OTHER INFORMATION: n is a, c, g, or t

<400> SEQUENCE: 12 nnngctt                                                                 7

<210> SEQ ID NO 13
<211> LENGTH: 7
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 13 nnagaaw                                                                 7

<210> SEQ ID NO 14
<211> LENGTH: 7
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 14 nnggaaw                                                                 7

<210> SEQ ID NO 15
<211> LENGTH: 7
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

```
<400> SEQUENCE: 15 nnaggaw                                                               7

<210> SEQ ID NO 16
<211> LENGTH: 7
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 16 nnagggw                                                               7

<210> SEQ ID NO 17
<211> LENGTH: 22
<212> TYPE: DNA
<213> ORGANISM: Artificial sequence
<220> FEATURE:
<223> OTHER INFORMATION: Synthetic

<400> SEQUENCE: 17
gtggcgtgac ctgtggatgc tg                                             22

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
ggttagggtt agggttaggg                                                20

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
agggttaggg ttagggttag                                                20

<210> SEQ ID NO 20
<211> LENGTH: 20
<212> TYPE: DNA
<213> ORGANISM: Artificial sequence
<220> FEATURE:
<223> OTHER INFORMATION: Synthetic

<400> SEQUENCE: 20
gttagggtta gggttagggt                                                20

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21
ttagggttag ggttagggtt                                                20
```

```
<210> SEQ ID NO 22
<211> LENGTH: 17
<212> TYPE: DNA
<213> ORGANISM: Artificial sequence
<220> FEATURE:
<223> OTHER INFORMATION: Synthetic

<400> SEQUENCE: 22
gggttagggt tagggtt                                                  17

<210> SEQ ID NO 23
<211> LENGTH: 13
<212> TYPE: DNA
<213> ORGANISM: Artificial sequence
<220> FEATURE:
<223> OTHER INFORMATION: Synthetic

<400> SEQUENCE: 23
tagggttagg gtt                                                      13

<210> SEQ ID NO 24
<211> LENGTH: 9
<212> TYPE: DNA
<213> ORGANISM: Artificial sequence Synthetic
<220> FEATURE:
<223> OTHER INFORMATION: Synthetic

<400> SEQUENCE: 24 gttagggtt                                                            9

<210> SEQ ID NO 25
<211> LENGTH: 6
<212> TYPE: DNA
<213> ORGANISM: Artificial sequence
<220> FEATURE:
<223> OTHER INFORMATION: Synthetic

<400> SEQUENCE: 25 agggtt                                                               6

<210> SEQ ID NO 26
<211> LENGTH: 20
<212> TYPE: DNA
<213> ORGANISM: Artificial sequence
<220> FEATURE:
<223> OTHER INFORMATION: Synthetic

<400> SEQUENCE: 26
tggaatggaa tggaatggaa                                               20

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
tgtctgtgag gaagctcccc                                               20

<210> SEQ ID NO 28
<211> LENGTH: 20
<212> TYPE: DNA
<213> ORGANISM: Artificial sequence
<220> FEATURE:
<223> OTHER INFORMATION: Synthetic
```

<400> SEQUENCE: 28
taagcatgga ccattccttc                                                   20

<210> SEQ ID NO 29
<211> LENGTH: 18
<212> TYPE: DNA
<213> ORGANISM: Artificial sequence
<220> FEATURE:
<223> OTHER INFORMATION: Synthetic

<400> SEQUENCE: 29
gggccaggac ctctaaaa                                                     18

<210> SEQ ID NO 30
<211> LENGTH: 18
<212> TYPE: DNA
<213> ORGANISM: Artificial sequence
<220> FEATURE:
<223> OTHER INFORMATION: Synthetic

<400> SEQUENCE: 30
ccggggaagt gctgagtc                                                     18

<210> SEQ ID NO 31
<211> LENGTH: 18
<212> TYPE: DNA
<213> ORGANISM: Artificial sequence
<220> FEATURE:
<223> OTHER INFORMATION: Synthetic

<400> SEQUENCE: 31
tggtgggtgt agacacgg                                                     18

<210> SEQ ID NO 32
<211> LENGTH: 24
<212> TYPE: DNA
<213> ORGANISM: Artificial sequence
<220> FEATURE:
<223> OTHER INFORMATION: Synthetic

<400> SEQUENCE: 32
ggttagggtt agggttaggg ttag                                               24

<210> SEQ ID NO 33
<211> LENGTH: 24
<212> TYPE: DNA
<213> ORGANISM: Artificial sequence
<220> FEATURE:
<223> OTHER INFORMATION: Synthetic

<400> SEQUENCE: 33
gttagggtta gggttagggt tagg                                               24

<210> SEQ ID NO 34
<211> LENGTH: 20
<212> TYPE: DNA
<213> ORGANISM: Artificial sequence
<220> FEATURE:
<223> OTHER INFORMATION: Synthetic

<400> SEQUENCE: 34
atggaatgga atggaatgga                                                   20

<210> SEQ ID NO 35

```
<211> LENGTH: 24
<212> TYPE: DNA
<213> ORGANISM: Artificial sequence
<220> FEATURE:
<223> OTHER INFORMATION: Synthetic

<400> SEQUENCE: 35
tagggttagg gttagggtta gggt                                          24

<210> SEQ ID NO 36
<211> LENGTH: 24
<212> TYPE: DNA
<213> ORGANISM: Artificial sequence
<220> FEATURE:
<223> OTHER INFORMATION: Synthetic

<400> SEQUENCE: 36
ctccatcctg aaggaatggt ccat                                          24

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
ggttagggtt agggttaggg                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic

<400> SEQUENCE: 38
atggaatgga atggaatgga                                               20

<210> SEQ ID NO 39
<211> LENGTH: 16
<212> TYPE: DNA
<213> ORGANISM: Artificial Sequence
<220> FEATURE:
<223> OTHER INFORMATION: Synthetic

<400> SEQUENCE: 39
ttagggttag ggttag                                                   16

<210> SEQ ID NO 40
<211> LENGTH: 28
<212> TYPE: DNA
<213> ORGANISM: Artificial Sequence
<220> FEATURE:
<223> OTHER INFORMATION: Synthetic

<400> SEQUENCE: 40
ctaaccctaa ccctaaccct aaccctaa                                      28

<210> SEQ ID NO 41
<211> LENGTH: 99
<212> TYPE: DNA
<213> ORGANISM: Artificial Sequence
<220> FEATURE:
<223> OTHER INFORMATION: Synthetic

<400> SEQUENCE: 41
```

```
guuaggguua ggguuagggu uguuugagag cuagaaaaua gcaagucaaa uaaggcuagu    60
ccguuaucaa cuugaaaaag uggcaccgag ucggugcuu                           99
```

<210> SEQ ID NO 42
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: N represents a repeat of GGGGCC with 0 to 100
      repeats

<400> SEQUENCE: 42

```
ggggccgggg ccggggccgg ggccggggcc nggggccggg ccggggccg gggccggggc    60 c                                                                    61
```

<210> SEQ ID NO 43
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: N is a repeat of GGCCCC with 0 to 100 repeats

<400> SEQUENCE: 43

```
ccggggggcc ccggccccgg ccccggcccc nggccccggc ccggccccg gccccggccc    60 c                                                                    61
```

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44

```
ccggggccgg ggccggggcc ggg                                            23
```

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45

```
cccggccccg gccccggccc                                                20
```

<210> SEQ ID NO 46
<211> LENGTH: 14
<212> TYPE: DNA
<213> ORGANISM: Artificial Sequence
<220> FEATURE:
<223> OTHER INFORMATION: Synthetic

<400> SEQUENCE: 46

```
tgatatcaca gtgg                                                      14
```

```
<210> SEQ ID NO 47
<211> LENGTH: 14
<212> TYPE: DNA
<213> ORGANISM: Artificial Sequence
<220> FEATURE:
<223> OTHER INFORMATION: Synthetic

<400> SEQUENCE: 47
tgatatcaga gtgg                                                        14

<210> SEQ ID NO 48
<211> LENGTH: 14
<212> TYPE: DNA
<213> ORGANISM: Artificial Sequence
<220> FEATURE:
<223> OTHER INFORMATION: Synthetic

<400> SEQUENCE: 48
tgatatcata gtgg                                                        14

<210> SEQ ID NO 49
<211> LENGTH: 14
<212> TYPE: DNA
<213> ORGANISM: Artificial Sequence
<220> FEATURE:
<223> OTHER INFORMATION: Synthetic

<400> SEQUENCE: 49
tgatatcaaa gtgg                                                        14

<210> SEQ ID NO 50
<211> LENGTH: 14
<212> TYPE: DNA
<213> ORGANISM: Artificial Sequence
<220> FEATURE:
<223> OTHER INFORMATION: Synthetic

<400> SEQUENCE: 50
tgatatgaca gtgg                                                        14

<210> SEQ ID NO 51
<211> LENGTH: 14
<212> TYPE: DNA
<213> ORGANISM: Artificial Sequence
<220> FEATURE:
<223> OTHER INFORMATION: Synthetic

<400> SEQUENCE: 51
tgatattaca gtgg                                                        14

<210> SEQ ID NO 52
<211> LENGTH: 14
<212> TYPE: DNA
<213> ORGANISM: Artificial Sequence
<220> FEATURE:
<223> OTHER INFORMATION: Synthetic
```

-continued

```
<400> SEQUENCE: 52
tgatataaca gtgg                                                          14

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gacaucgaug uccucccau                                                     20
```